(12) United States Patent
Cooper et al.

(10) Patent No.: US 11,399,711 B2
(45) Date of Patent: Aug. 2, 2022

(54) CEREBROVASCULAR PATHOLOGY VIEWING AND TREATMENT APPARATUS

(71) Applicant: Vena Medical Holdings Corp., Kitchener (CA)

(72) Inventors: Phillip Cooper, Pembroke (CA); Michael Phillips, Elmira (CA)

(73) Assignee: Vena Medical Holdings Corp., Kitchener (CA)

( * ) Notice: Subject to any disclaimer, the term of this patent is extended or adjusted under 35 U.S.C. 154(b) by 0 days.

(21) Appl. No.: 17/359,078

(22) Filed: Jun. 25, 2021

(65) Prior Publication Data

US 2021/0321867 A1 Oct. 21, 2021

Related U.S. Application Data

(63) Continuation of application No. PCT/CA2020/050023, filed on Jan. 9, 2020.
(Continued)

(51) Int. Cl.
*A61B 1/00* (2006.01)
*A61B 1/313* (2006.01)
(Continued)

(52) U.S. Cl.
CPC .......... *A61B 1/3137* (2013.01); *A61B 1/0055* (2013.01); *A61B 1/00082* (2013.01);
(Continued)

(58) Field of Classification Search
CPC . A61B 1/3137; A61B 1/00082; A61B 1/0055; A61B 1/07; A61B 1/08;
(Continued)

(56) References Cited

U.S. PATENT DOCUMENTS 4,830,460 A * 5/1989 Goldenberg ....... A61B 1/00165
385/118
4,838,876 A 6/1989 Wong et al.
(Continued)

FOREIGN PATENT DOCUMENTS

CA 2934880 A1 7/2015
WO WO-2020142846 A1 7/2020

OTHER PUBLICATIONS

International Application Serial No. PCT/CA2020/050023, International Search Report dated Feb. 28, 2020, 5 pgs.
(Continued)

*Primary Examiner* — Alexandra L Newton
*Assistant Examiner* — Rynae E Boler
(74) *Attorney, Agent, or Firm* — Schwegman Lundberg & Woessner, P.A.

(57) ABSTRACT

Cerebrovascular treatment at an intracranial location beyond the petrous segment of the carotid artery can be challenging due to blood vessel size and tortuosity. First pass cerebrovascular thrombectomy success rate under only fluoroscopic guidance can be low (e.g., 25.1%) but an angioscope can help improve efficacy. A sheath catheter can be advanced toward the cerebrovascular pathology. Its distal balloon can be inflated. An angioscope can be inserted via its working lumen for viewing. The sheath catheter can have a stepped-down lateral profile and can extend the working channel a distance beyond the balloon. A dual concentric lumen structure can include an inner body and an outer body, defining an inflation lumen therebetween, with one or more portions of one or more layers stretched or cut or both, such as to provide bending flexibility. Reflow techniques can be used to help bond layers together.

26 Claims, 24 Drawing Sheets

Related U.S. Application Data

(60) Provisional application No. 62/790,330, filed on Jan. 9, 2019.

(51) Int. Cl.
- *A61B 1/005* (2006.01)
- *A61B 1/018* (2006.01)
- *A61B 1/07* (2006.01)
- *A61B 17/12* (2006.01)
- *A61B 17/22* (2006.01)
- *A61F 2/95* (2013.01)

(52) U.S. Cl.
CPC ............... *A61B 1/018* (2013.01); *A61B 1/07* (2013.01); *A61B 17/12113* (2013.01); *A61B 2017/22079* (2013.01); *A61F 2002/9528* (2013.01)

(58) Field of Classification Search
CPC .... A61B 2017/22079; A61M 25/0053; A61M 25/0054; A61M 25/0051; A61M 25/10
See application file for complete search history.

(56) References Cited

U.S. PATENT DOCUMENTS

| | | | |
|---|---|---|---|
| 4,896,941 A | 1/1990 | Hayashi et al. | |
| 5,121,740 A | 6/1992 | Uram | |
| 5,411,016 A | 5/1995 | Kume et al. | |
| 5,507,766 A * | 4/1996 | Kugo | A61M 25/104 606/95 |
| 5,571,151 A | 11/1996 | Gregory | |
| 6,375,637 B1 * | 4/2002 | Campbell | A61M 25/10 604/537 |
| 6,527,707 B1 | 3/2003 | Frische et al. | |
| 6,899,672 B2 | 5/2005 | Chin et al. | |
| 7,582,057 B2 | 9/2009 | Toriya et al. | |
| 8,622,994 B2 | 1/2014 | Wendlandt et al. | |
| 8,798,721 B2 | 8/2014 | Dib | |
| 2006/0058775 A1 * | 3/2006 | Stevens | A61B 17/3421 604/509 |
| 2008/0262308 A1 | 10/2008 | Prestezog et al. | |
| 2009/0076447 A1 * | 3/2009 | Casas | A61M 25/04 604/96.01 |
| 2009/0203962 A1 | 8/2009 | Miller | |
| 2010/0081873 A1 | 4/2010 | Tanimura et al. | |
| 2010/0217257 A1 * | 8/2010 | Howat | A61M 25/0012 606/41 |
| 2013/0253417 A1 * | 9/2013 | Dinh | A61M 25/0053 604/28 |
| 2015/0025562 A1 | 1/2015 | Dinh et al. | |
| 2015/0374217 A1 | 12/2015 | Sinofsky | |
| 2016/0174995 A1 * | 6/2016 | Turjman | A61B 17/22 606/127 |
| 2016/0346503 A1 * | 12/2016 | Jackson | A61M 25/0012 |
| 2017/0128695 A1 * | 5/2017 | Speiser | A61M 25/10181 |
| 2017/0265879 A1 | 9/2017 | Washburn, Ii et al. | |
| 2018/0140808 A1 * | 5/2018 | Kubo | A61M 25/0045 |
| 2018/0304040 A1 * | 10/2018 | Jalgaonkar | A61M 25/0054 |
| 2018/0326178 A1 * | 11/2018 | Moquin | A61L 29/085 |
| 2019/0381288 A1 * | 12/2019 | Mock | A61M 25/10 |

OTHER PUBLICATIONS

International Application Serial No. PCT/CA2020/050023, Written Opinion dated Feb. 28, 2020, 11 pgs.

* cited by examiner

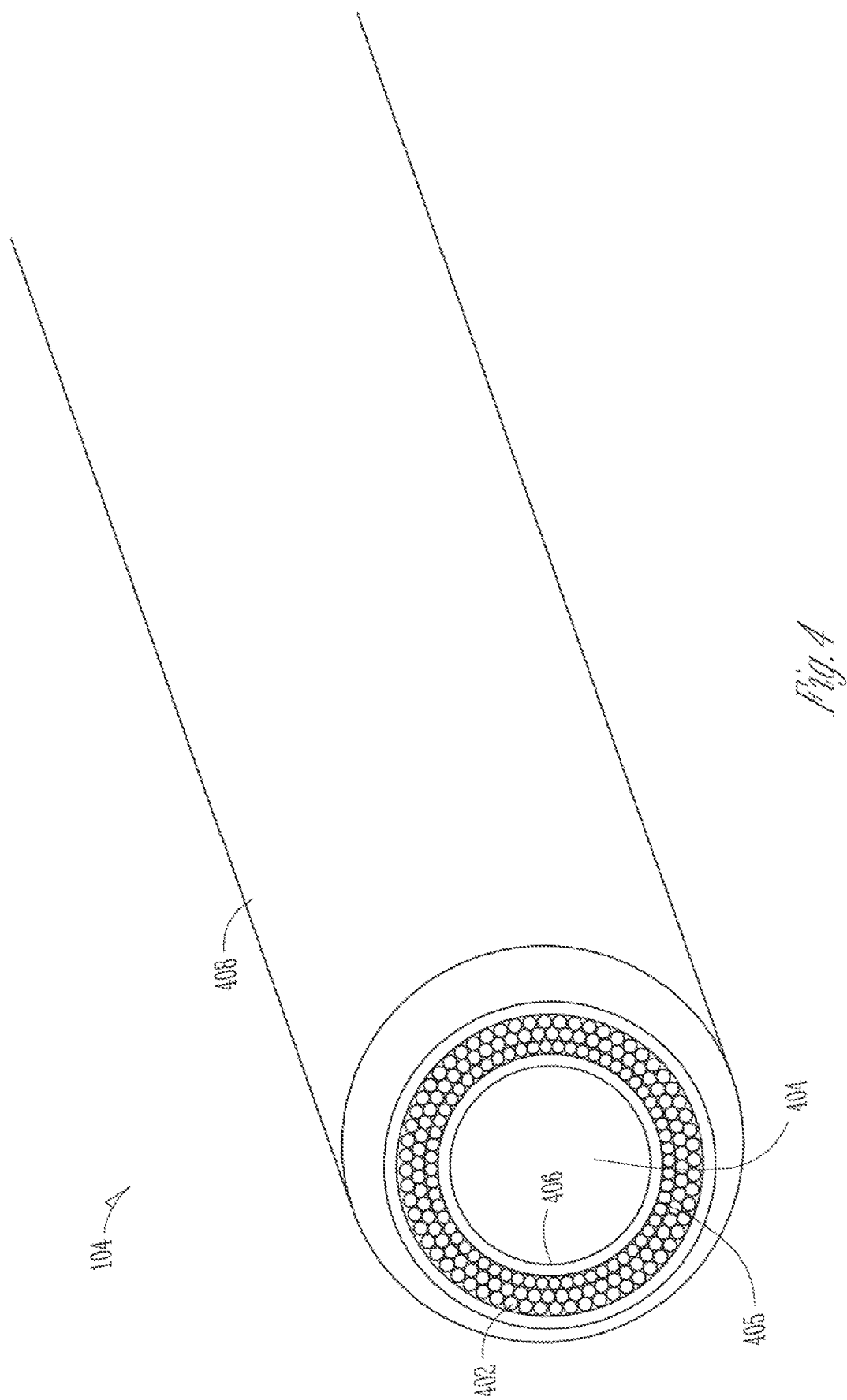

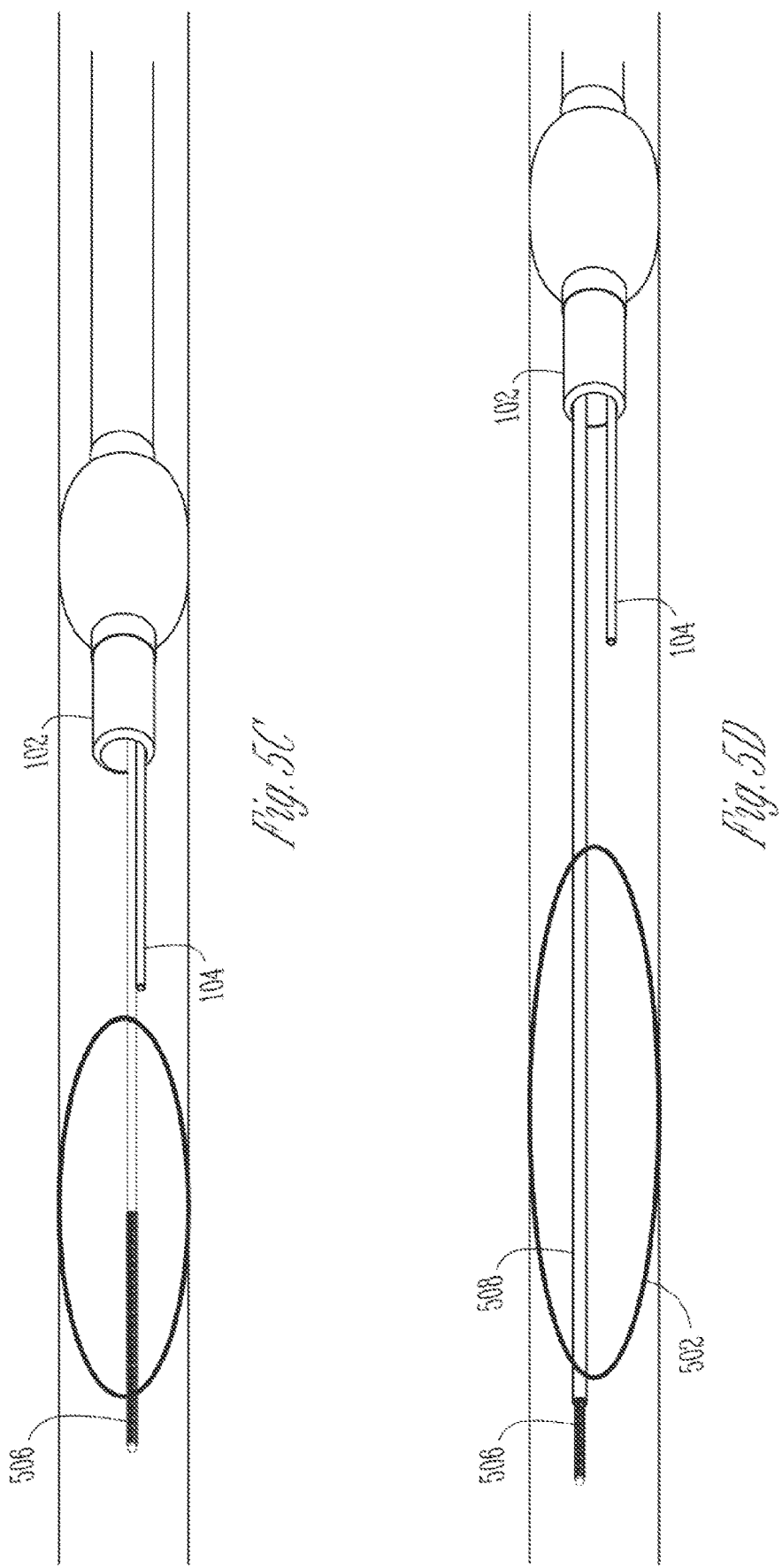

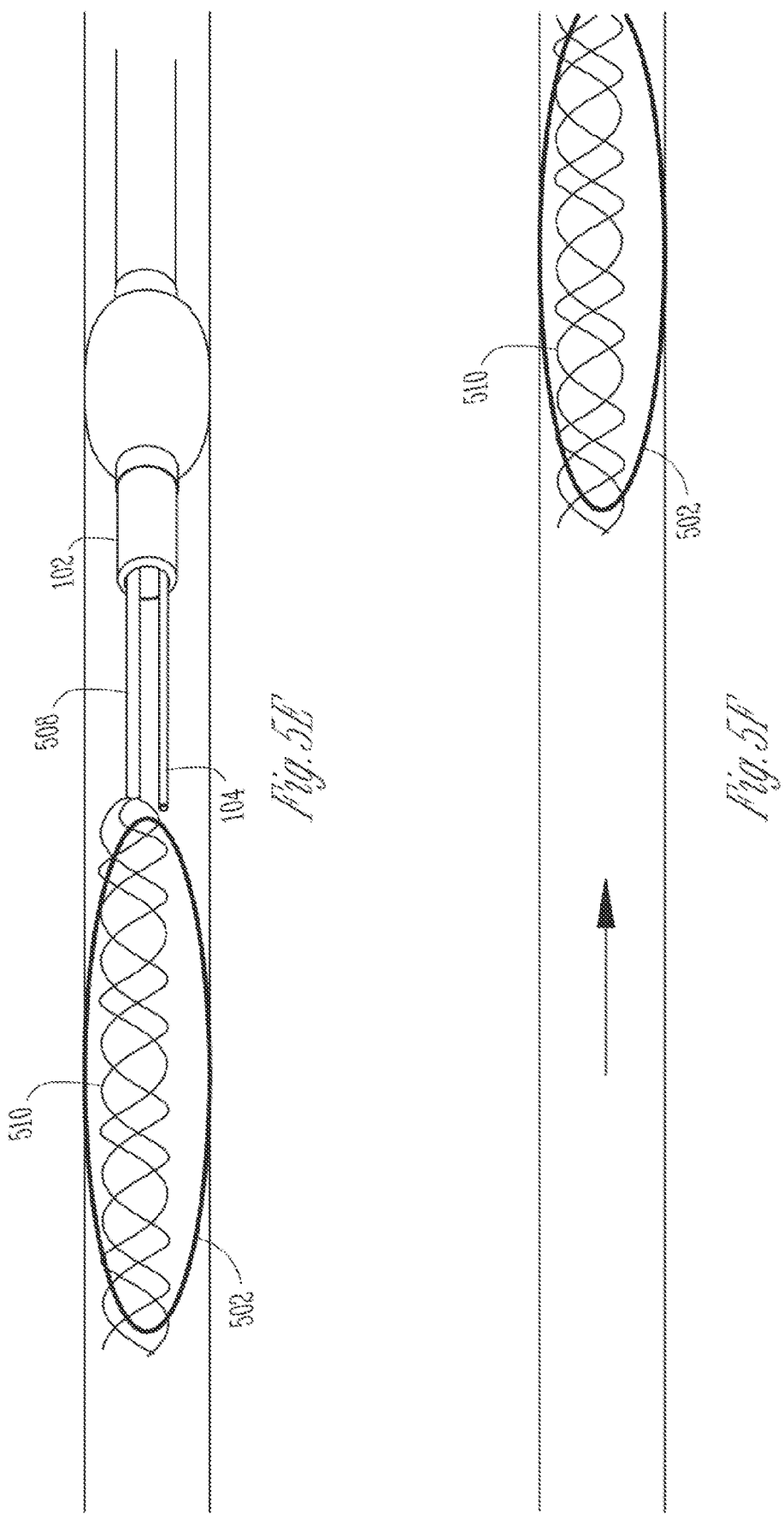

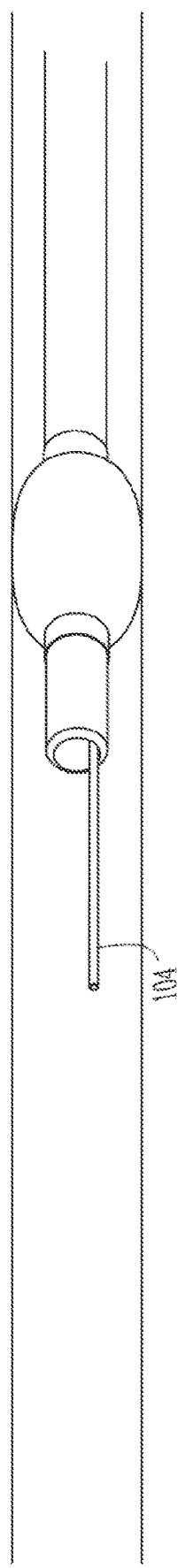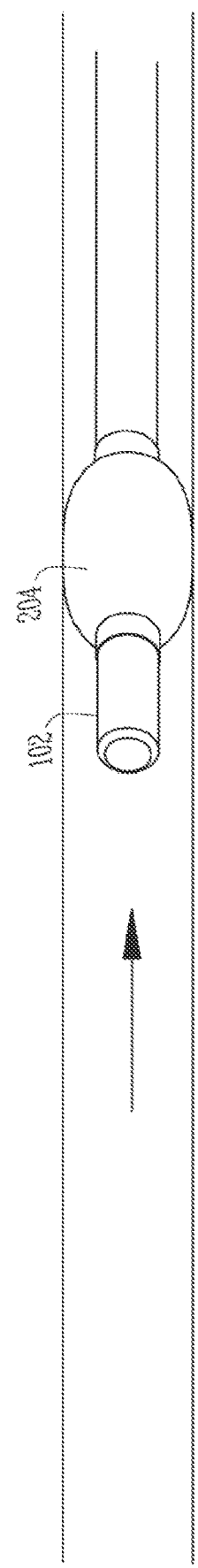
Fig. 6H
Fig. 6I

FIG. 6G

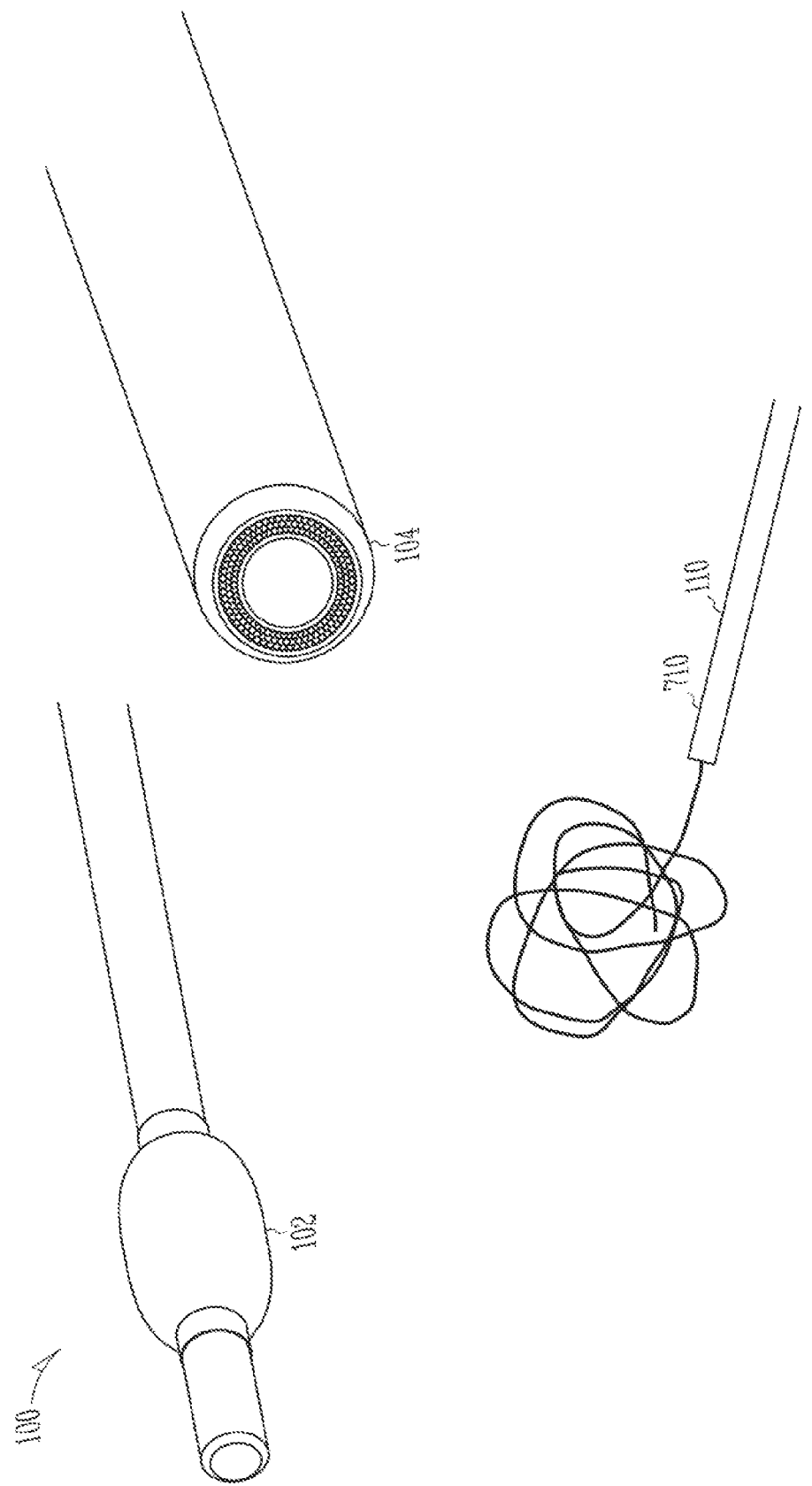

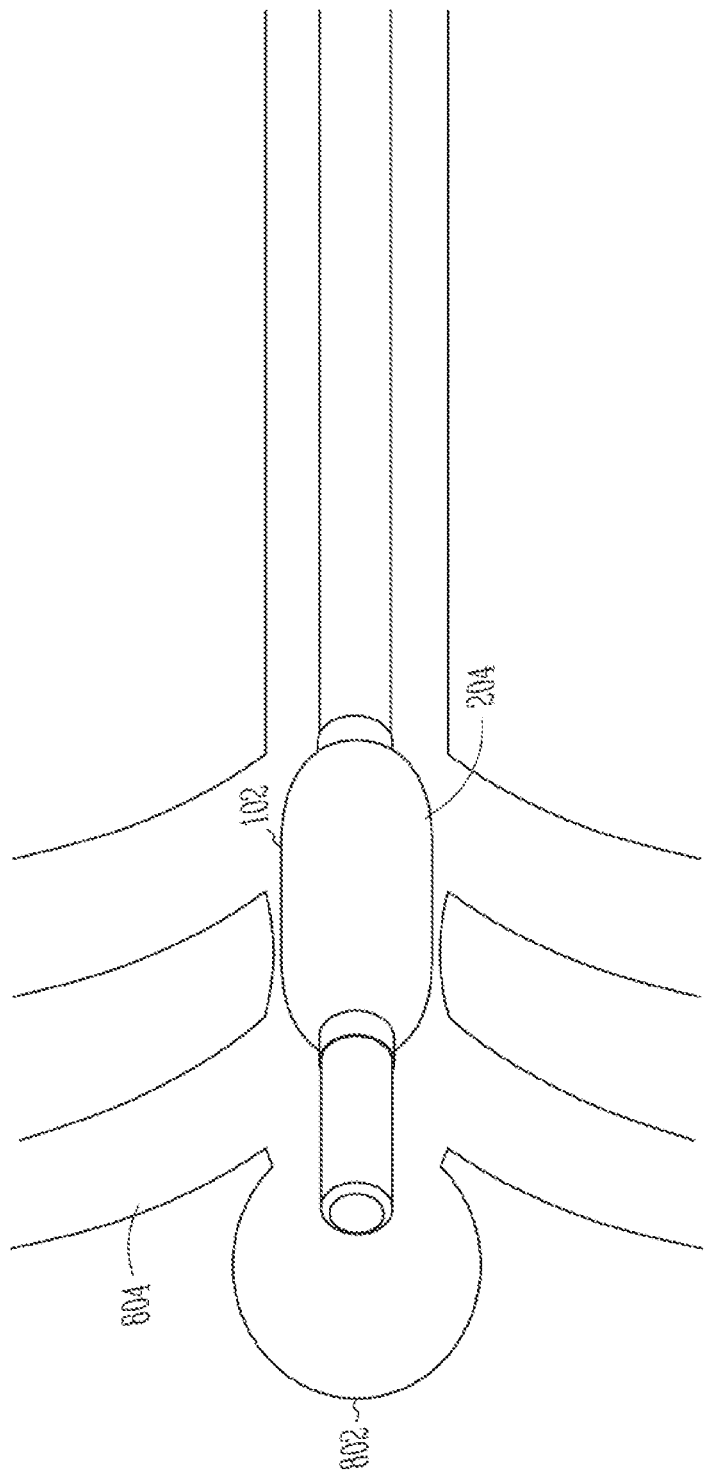

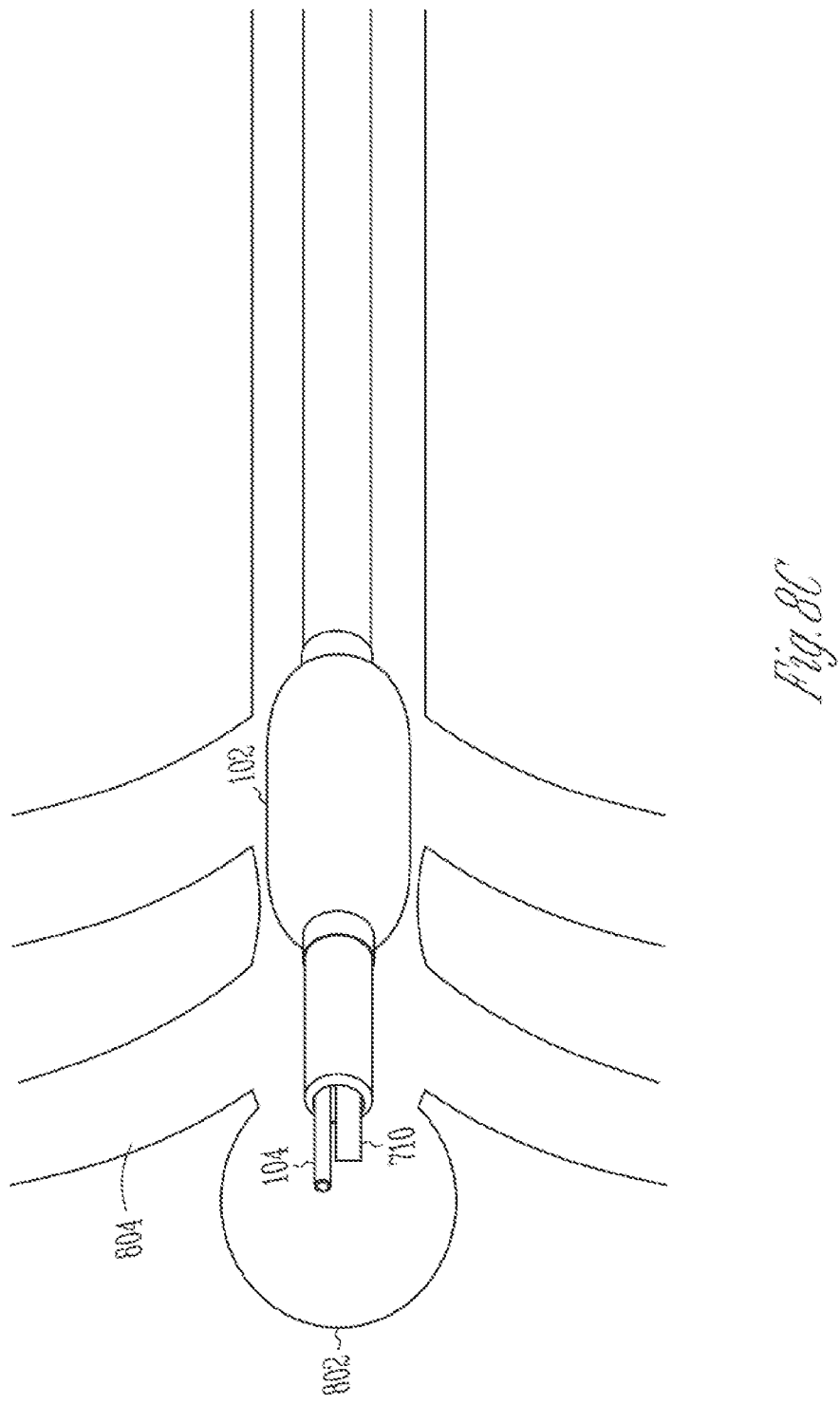

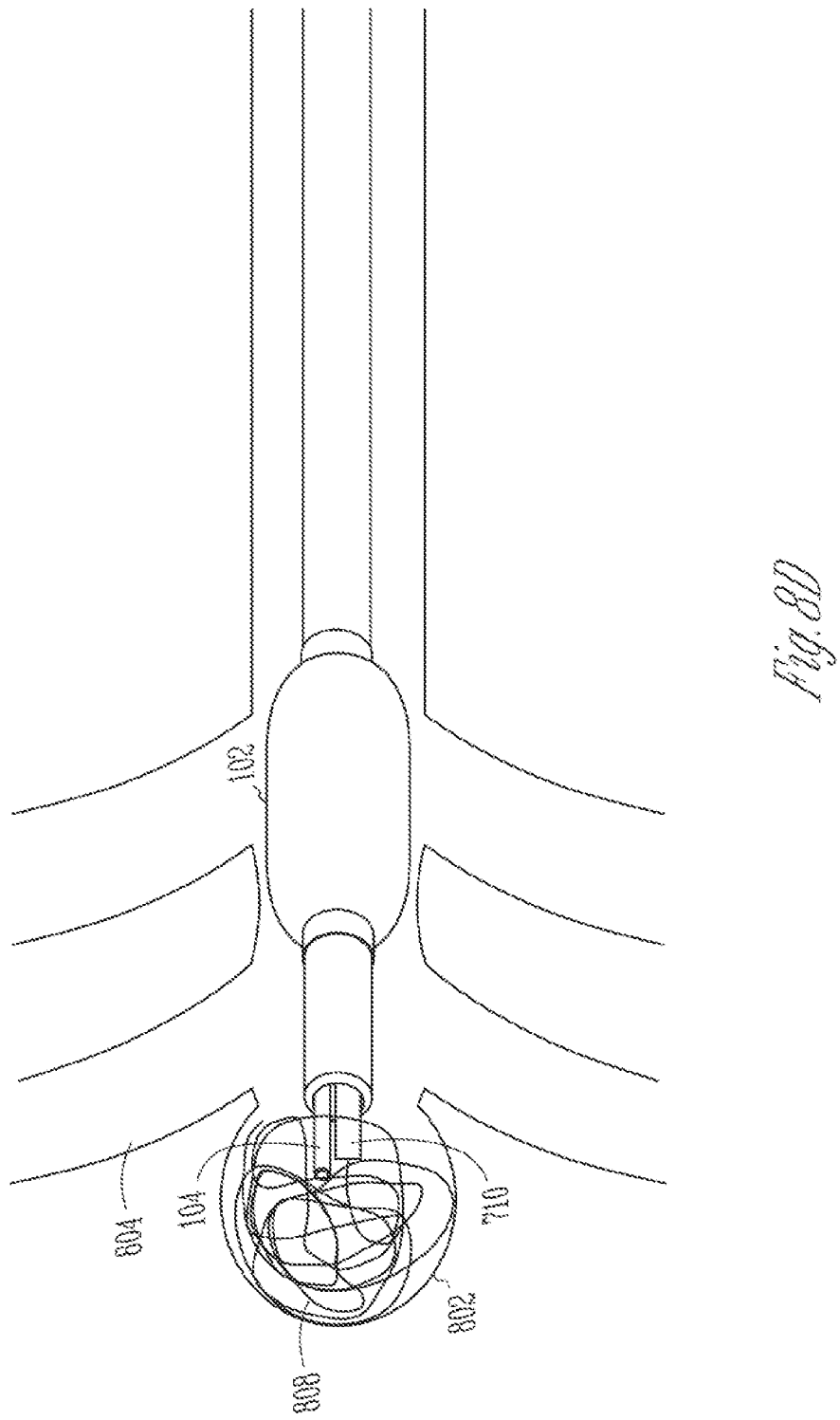

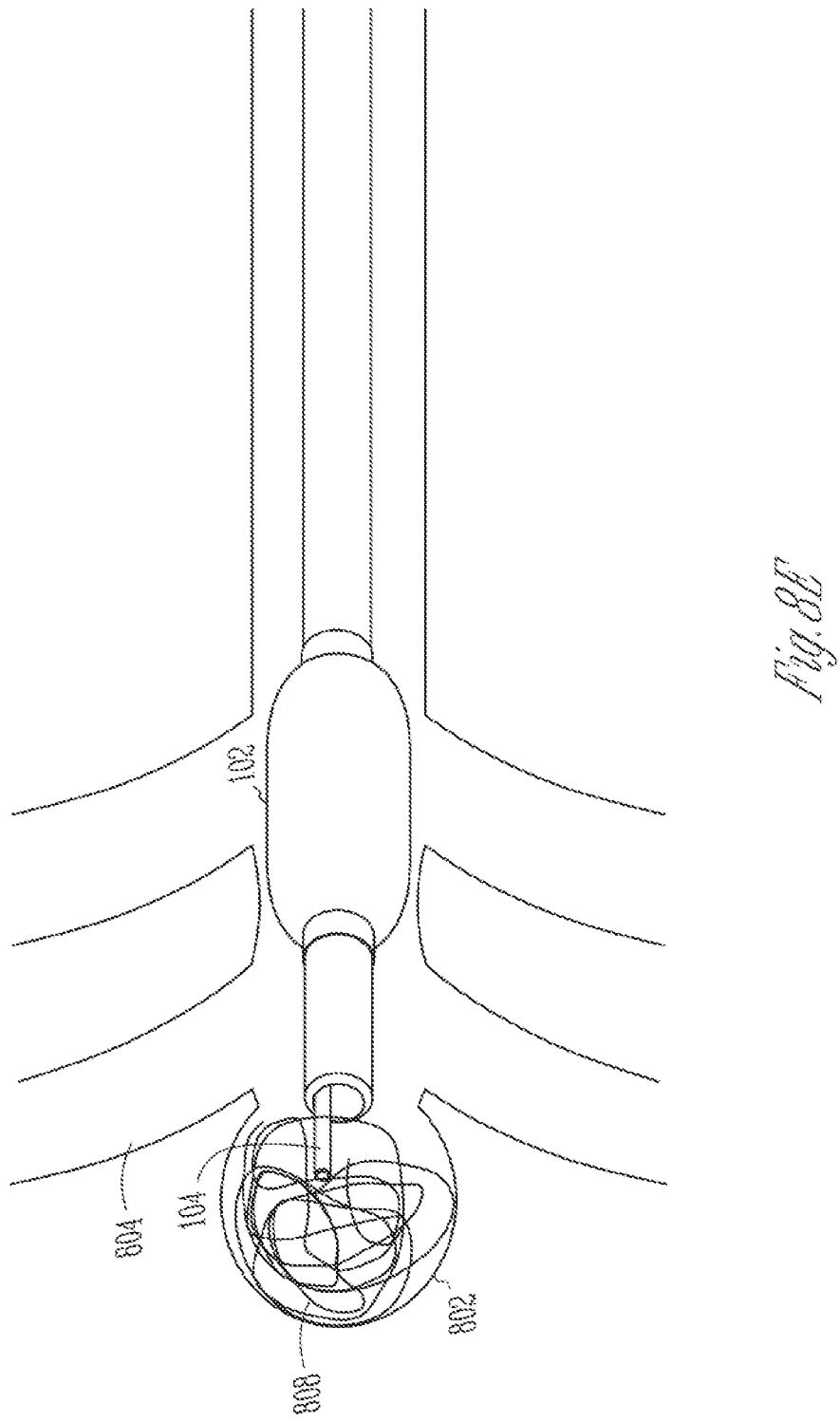

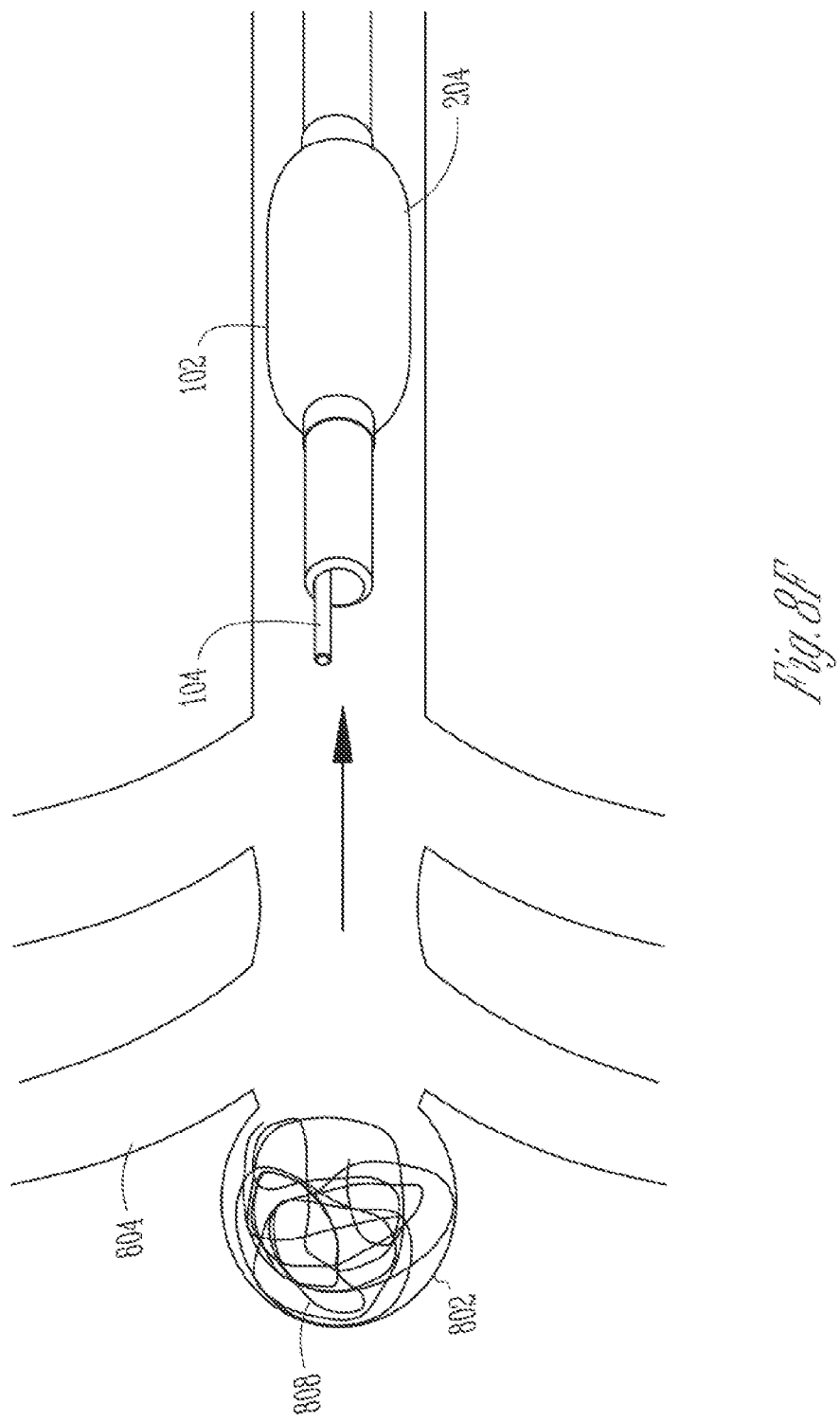

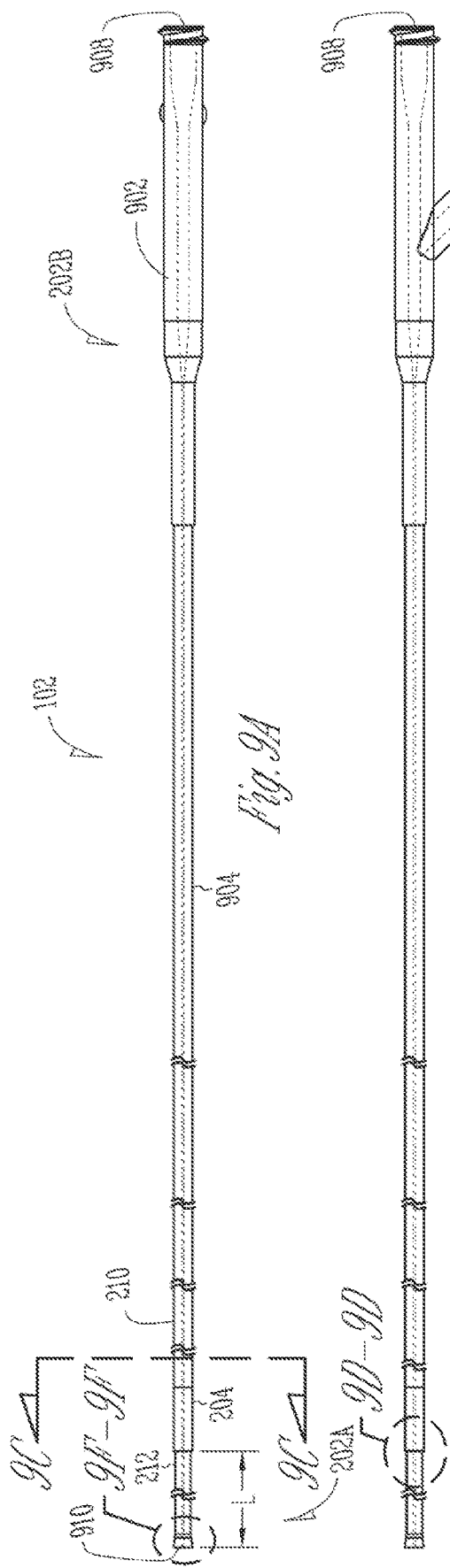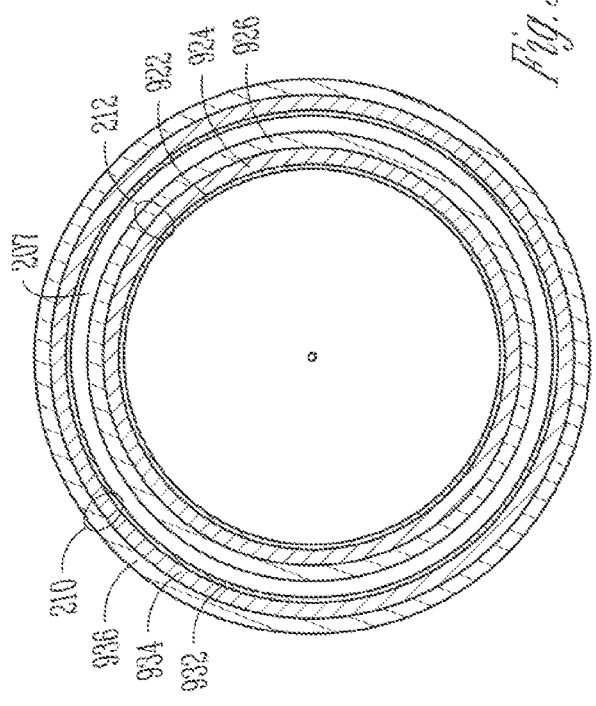

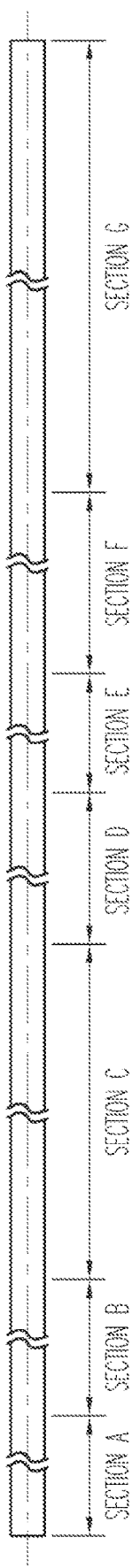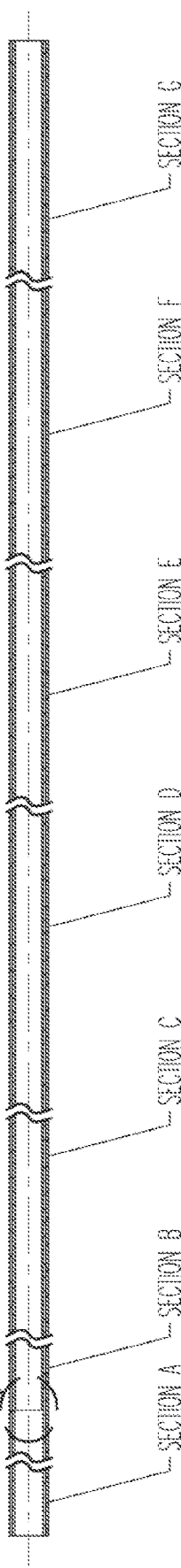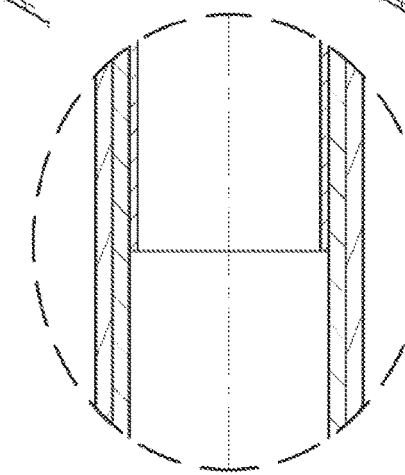
Fig. 10A
Fig. 10B
Fig. 10C

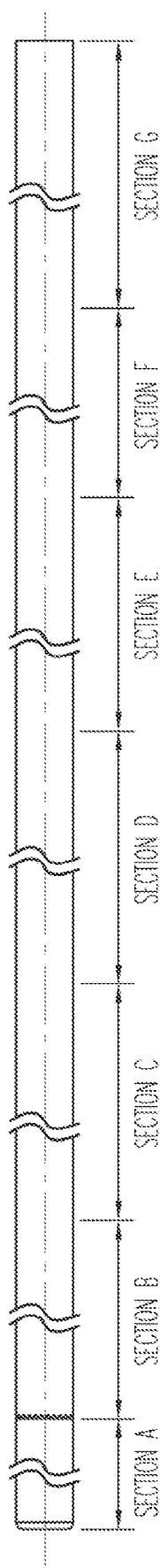
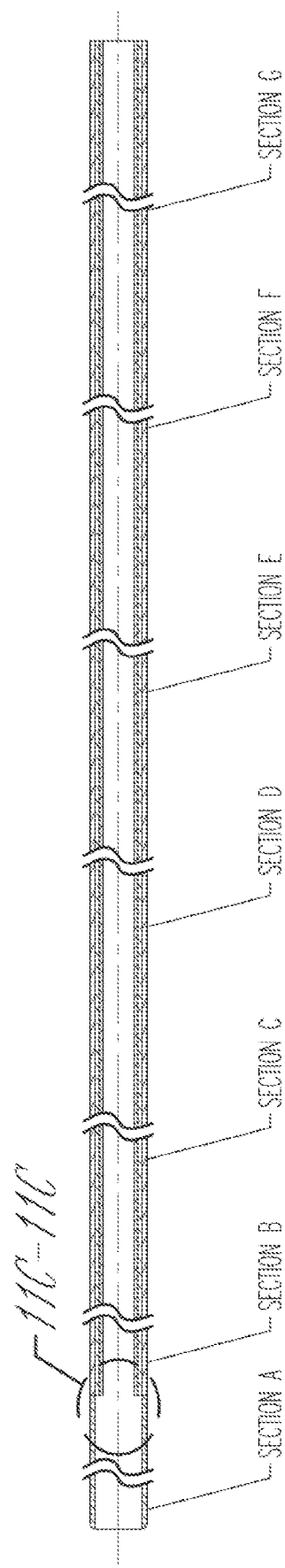
Fig. 11A
Fig. 11B
Fig. 11C

CEREBROVASCULAR PATHOLOGY VIEWING AND TREATMENT APPARATUS

CLAIM OF PRIORITY

This application is a continuation of and claims to benefit of priority under 35 U.S.C. § 120 to International Patent Application No. PCT/CA2020/050023, filed on Jan. 9, 2020, and also the benefit of priority of U.S. Provisional Patent Application Ser. No. 62/790,330, filed Jan. 9, 2019, each of which is incorporated by reference herein in its entirety.

TECHNICAL HELD

This document pertains generally, but not by way of limitation, to intravascular imaging and treatment and, more particularly, but not by way of limitation to cerebrovascular pathology viewing and treatment.

BACKGROUND

Cerebrovascular pathologies can include, among other things, a thrombus (blood clot) or an aneurysm (localized enlargement or weakening of a blood vessel). A cerebrovascular thrombus can be associated with ischemic stroke, which, in turn can cause damage to brain tissue. A cerebrovascular aneurysm can be associated with a risk of rupture and hemorrhagic stroke, which, in turn can also cause damage to brain tissue.

Radiographic fluoroscopic imaging from an imaging instrument location outside the patient can he used to guide an intravascular instrument within a patient's vasculature to a cerebrovascular pathology, such as for performing a treatment such as a thrombectomy or an aneurysm coiling. However, it can be difficult or impossible to assess the pathology or its composition or treatment using such external radiographic fluoroscopic imaging, which can also require using an iodinated contrast agent that must be introduced into the patient to be imaged. Such fluoroscopic image guidance of instrumentation has shortcomings. For example, the first pass attempt success rate of such a fluoroscopically-guided cerebrovascular thrombectomy is low; one study places it at only 25.1%. Further, radiation induced complications of such fluoroscopy to the patient can include skin burns and hair loss, which can occur at doses as low as 3 Gy. Still further, contrast-related nephropathy in patients has been reported to occur in approximately 20-30% of patients with pre-existing renal disease and up to 5% of other low-risk patients. In addition to the radiation risk to the patient, there also exists a radiation risk to the operator of the radiographic fluoroscopic imaging apparatus. Even with proper shielding and attire, radiation risk to the operator is not trivial, with reports of up to 254 Gy of radiation to the operator's hands and eyes per case. Also, for the operator, the dose is cumulative throughout the operator's career. Even further, such indirect visualization using a radiographic fluoroscopic imaging apparatus in cases with difficult anatomy can contribute to malpositioned treatment devices, which, in the case of cerebrovascular pathologies, can lead to thromboembolic and hemorrhagic complications to the patient.

SUMMARY

The present inventors have recognized, among other things, an unmet need for devices and methods that can help enable real-time, full color, diagnostic quality resolution intravascular direct visualization of a cerebrovascular pathology that can be located within intracranial vasculature, such as before, during, or after intravascular treatment of the cerebrovascular pathology. This can permit, for example, intravascular direct visualization viewing and treatment of a cerebrovascular thrombus before a thrombectomy such as to permit assessing thrombus color or composition to guide treatment, during the thrombectomy such as to guide treatment, or after the thrombectomy such as to assess results or determine further treatment can help improve treatment efficacy or speed or help avoid one or more side-effects. In another example, the present devices and methods can help permit intravascular viewing and treatment of a cerebrovascular aneurysm, such as before aneurysm treatment using a thrombolytic occluder (such as coils, a thrombogenic agent, or both) such as to plan or guide such treatment, during such aneurysm treatment such as to help guide in real-time performing or adjusting or adapting such treatment, or after such aneurysm treatment, such as to help assess efficacy of the treatment delivered or to guide further planning or treatment.

A cerebrovascular pathology located within intracranial vasculature can present a particularly challenging environment, such as due to one or more of small vessel size, tortuous vessel morphology, or time-constraints on diagnostic or therapeutic vascular instrumentation or intervention, such as due to the risk of side-effects to brain tissue by diminished blood flow or perfusion due to the cerebrovascular pathology or intravascular diagnostic or treatment apparatuses introduced to diagnose or treat such a cerebrovascular pathology. Certain intravascular imaging techniques, such as intravascular ultrasound (IVUS) or optical coherence tomography (OCT) can present shortcomings in a cerebrovascular pathology diagnosis or treatment application, such as lack of direct visualization and viewing or lack of sufficient miniaturization to be compatible with use within small and tortuous intracranial vasculature. Other techniques, such as a scanning fiber endoscope (SFE) can offer direct visualization, as compared to the indirect imaging of IVUS or OCT, but can be difficult to miniaturize to reach a cerebrovascular pathology at an intracranial location such as beyond the petrous segment of the carotid artery.

This document describes, among other things, a forward-viewing fiberoptic angioscope such as can include illumination fibers and Coherent Fiber Bundle (CFB) imaging fibers, such as can be suitable for intravascular direct visualization at its distal end of a cerebrovascular pathology at an intracranial location beyond the petrous segment of the carotid artery in small and tortuous blood vessels. The angioscope can be used within a working lumen of a sheath catheter, such as to forwardly view and inspect the pathology using the angioscope. The sheath catheter can have an outer diameter between 3.5 French (1.17 millimeters) and 8.0 French (2.67 millimeters), and can define an inner diameter of the working lumen of the sheath catheter being in a range between 0.039 inches (0.99 millimeters) and 0.082 inches (2.08 millimeters), inclusive, such as a nominal or preferred value of about 0.070 inches (1.78 millimeters). This can permit at least a portion of the cerebrovascular pathology treatment catheter and at least a portion of the angioscope to both be located within the working lumen of the sheath catheter.

The sheath catheter can optionally include a distal balloon near its distal portion, such as set back from a distal end tip of the sheath catheter. The distal balloon can be inflated, such as by introducing a liquid into a port at a proximal end of the sheath catheter, which can be communicated to the balloon via one or more inflation lumens extending from the proximal port to the distal balloon. Inflating the balloon can help stabilize the sheath catheter within the vasculature, such as at an intracranial location such as beyond the petrous segment of the carotid artery near the cerebrovascular pathology.

The sheath catheter can have a stepped-down lateral profile and can extend the working channel a distance beyond the balloon. A dual concentric lumen structure can include an inner body and an outer body, defining an inflation lumen therebetween, with one or more portions of one or more layers stretched or cut or both, such as to provide bending flexibility. Reflow techniques can be used to help bond layers together.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4 is a schematic illustrating an example of portions of an angioscope.

FIGS. 5A, 5B, 5C, 5D, 5E, 5F, 5G, 5H, and 5I illustrate an example of a method of using one or more portions of the system for a stent retriever thrombectomy under viewing by the angioscope, FIGS. 6A, 6B, 6C, 6D, 6E, 6F, and 6G illustrate an example of a method of using one or more portions of the system for an aspiration-based thrombectomy under viewing by the angioscope.

FIG. 7 shows an example of portions of a cerebrovascular or other intravascular pathology treatment kit or system, similar to that shown in FIG. 1, but including an optional cerebrovascular or other intravascular pathology treatment catheter that can include a. thrombolytic occlusion device, such as a coil deployment catheter.

FIGS. 8A, 8B, 8C, 8D, 8E, and 8F illustrate an example of a method of using one or more portions of the system for aneurysm treatment under viewing by the angioscope.

FIGS. 9A, 9B, 9C, 9D, 9E, and 9F builds upon the description of earlier-presented figures, and show various views of portions of an example of a sheath catheter.

FIGS. 10A (side view) and 10B (side sectional view) and 10C (detailed side sectional view at the line 10C-10C of FIG. 10B) shows an example of the inner body or inner sheath, together with an illustrative example of its layered construction along a length of the elongate body of the sheath catheter.

FIGS. 11A (side view) and 11B (side sectional view) and 11C (detailed side sectional view at the line 11C-11C of FIG. 11B) shows an example of the outer body or outer sheath, together with an illustrative example of its layered construction along a length of the elongate body of the sheath catheter.

DETAILED DESCRIPTION

The present devices and methods can help enable real-time, full color, diagnostic quality resolution intravascular visualization of a cerebrovascular pathology, such as before, during, or after intravascular treatment of the cerebrovascular pathology. This can permit, for example, intravascular viewing and treatment of a cerebrovascular thrombus before a thrombectomy such as to permit assessing thrombus color or composition to guide treatment, during the thrombectomy such as to guide treatment, or after the thrombectomy such as to assess results or determine further treatment can help improve treatment efficacy or speed or help avoid one or more side-effects. In another example, the present devices and methods can help permit intravascular viewing and treatment of a cerebrovascular aneurysm, such as before aneurysm treatment using a thrombolytic occluder (such as coils, a thrombogenic agent, or both) such as to plan or guide such treatment, during such aneurysm treatment such as to help guide in real-time performing or adjusting or adapting such treatment, or after such aneurysm treatment, such as to help assess efficacy of the treatment delivered or to guide further planning or treatment. While one study places the first pass attempt success rate of a cerebrovascular thrombectomy guided only by external radiographic fluoroscopy at 25.1%, the present systems, devices, and techniques employing real-time visualization using an angioscope were used in an animal model study in which 8 of 8 first pass thrombectomy attempts were successful, yielding a success rate of 100% for this limited animal model study.

The angioscope or other instruments can be used with a sheath catheter. The sheath catheter can optionally include a distal balloon near its distal portion, such as set back from a distal end tip of the sheath catheter. The distal balloon can be inflated, such as by introducing a liquid into a port at a proximal end of the sheath catheter, which can be communicated to the balloon via one or more inflation lumens extending from the proximal port to the distal balloon. Inflating the balloon can help stabilize the sheath catheter within the vasculature, such as at an intracranial location such as beyond the petrous segment of the carotid artery near the cerebrovascular pathology. The sheath catheter can have a stepped-down lateral profile and can extend the working channel a distance beyond the balloon. A dual concentric lumen structure can include an inner body and an outer body, defining an inflation lumen therebetween, with one or more portions of one or more layers stretched or cut or both, such as to provide bending flexibility. Reflow techniques can be used to help bond layers together.

Figure 1:
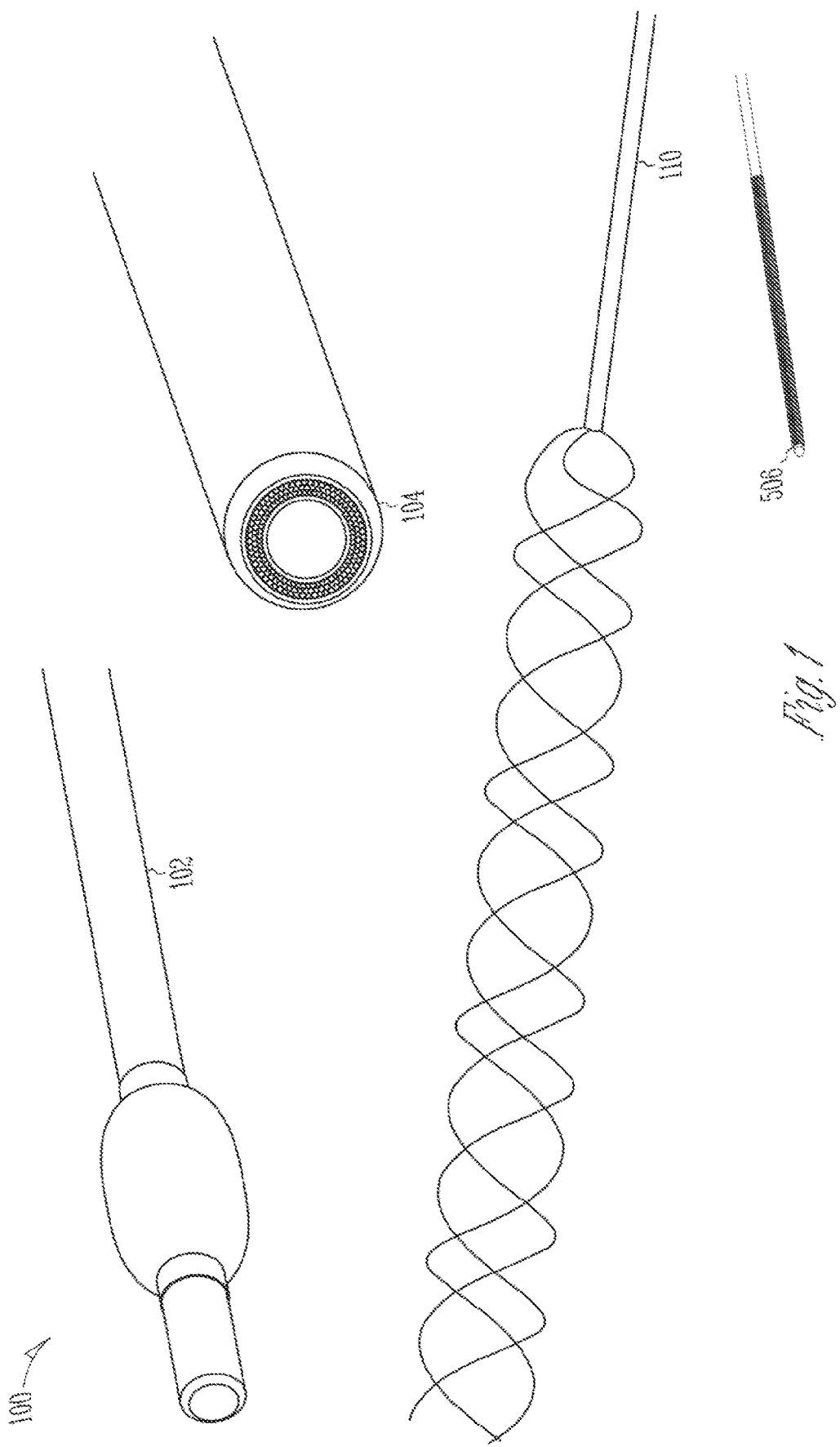
FIG. 1 shows an example of portions of a cerebrovascular or other intravascular pathology treatment kit or system.

FIG. 1 shows an example of portions of a cerebrovascular or other intravascular pathology treatment kit or system 100, such as can include one or more of a distal access balloon guide sheath catheter or other sheath catheter 102, a microangioscope 104, and an optional cerebrovascular or other intravascular pathology treatment catheter 106. The sheath catheter 102 can include an elongate body that can define an inner working lumen 108, such as can extend from a. proximal opening at a proximal end or a proximal portion of the sheath catheter 106 to a distal opening at a distal end or a distal portion of the sheath catheter 106. As explained further herein, the working lumen 108 of the sheath catheter 102 can define an inner diameter that can be sized to permit at least a portion of both the angioscope 104 and the treatment catheter 106 to be located within the inner working lumen 108 together, such as can permit concurrent visualization using the angioscope 104 and intravascular treatment using the treatment catheter 106. One or more other components can also optionally be included in or used with the system 100, such as a guidewire, such as can be used to help intravascularly introduce the sheath catheter 102, the treatment catheter 106, or both, such as toward a desired distal location within a human patient or subject, such as to a cerebrovascular location beyond the petrous segment of the carotid artery of the subject. Examples of the pathology treatment catheter 106 or other instruments or materials that can be used or accommodated within the working lumen 108 of the sheath catheter 108 can include, among other things, one or more guidewires, microcatheters, stent retrievers, saline (e.g., as a flushing agent for displacing opaque blood to permit distal viewing via the angioscope 104), contrast agent, blood clots, aneurysm coils, or any combination of these. For example, the pathology treatment catheter 106 can include a commercially available stent retriever catheter configured for distally engaging and retrieving a blood clot. Such a stent retriever catheter can include a guidewire lumen such as to allow the stent retriever catheter 106 to be inserted to a desired location in the vasculature over the wire (OTW), such as to a thrombus that has been penetrated or crossed by the guidewire over which the stent retriever catheter 106 is introduced.

Figure 2:
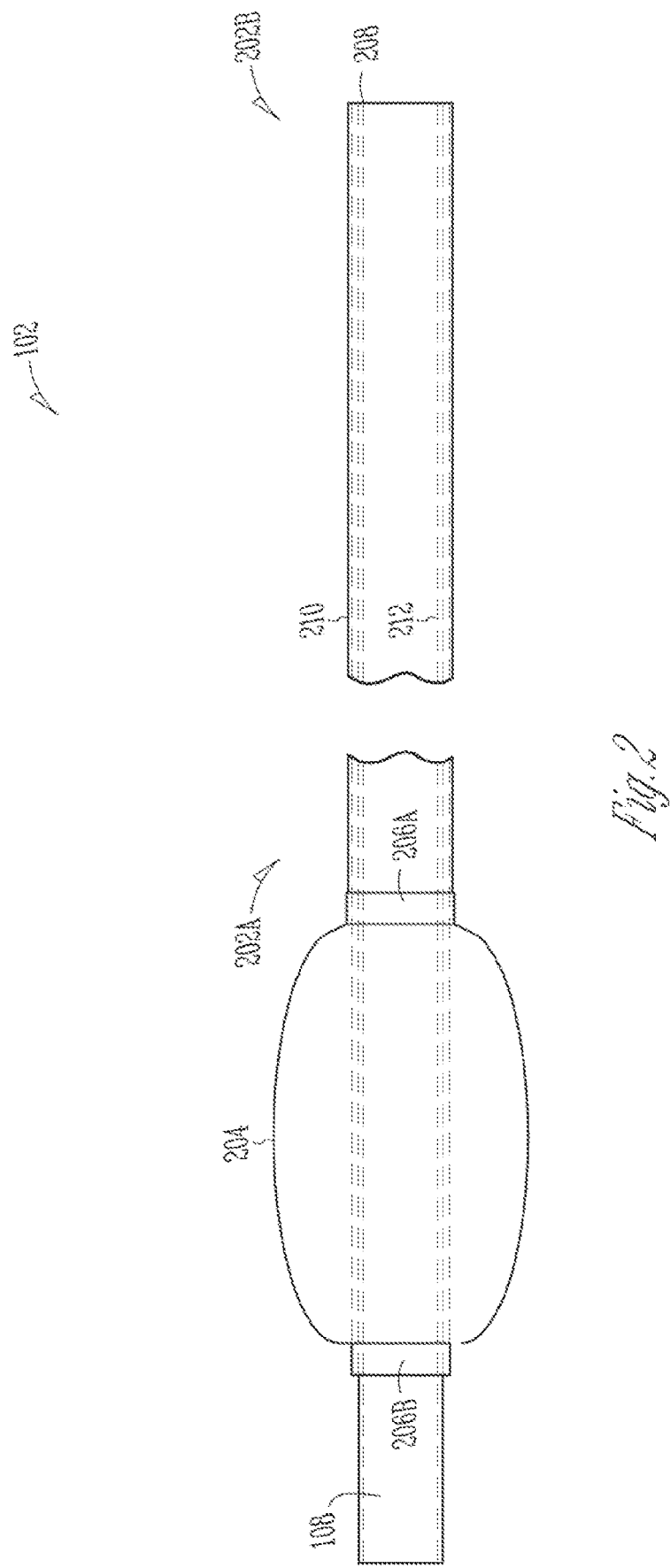
FIG. 2 shows a more detailed example of portions of a sheath catheter, including an elongate body having a distal portion and a proximal portion.
Figure 3:
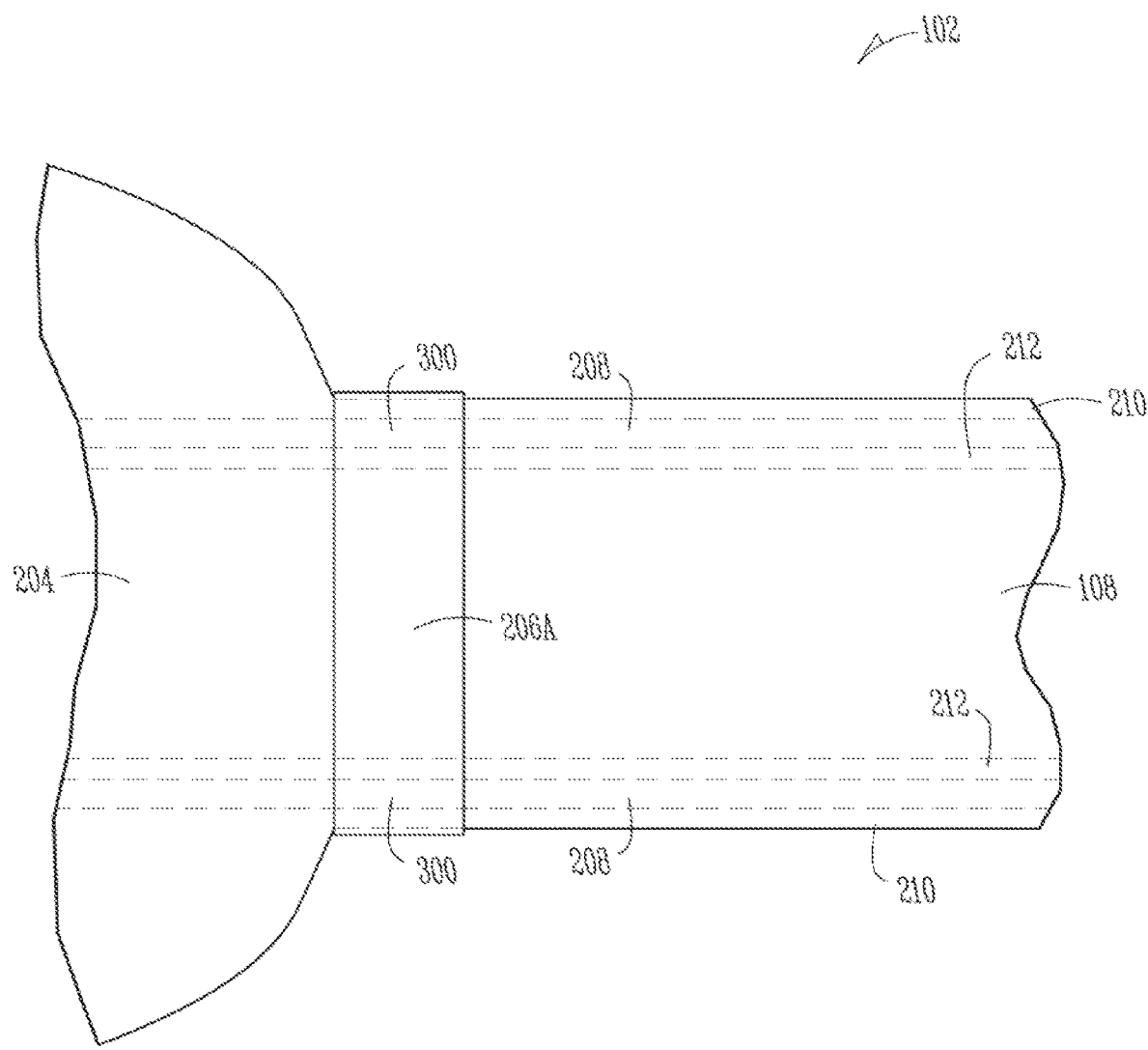
FIG. 3 shows a closer view of the "Detail A" region of FIG. 2.

FIG. 2 shows a more detailed example of portions of the sheath catheter 102, including an elongate body having a distal portion 202A and a proximal portion 202B. FIG. 3 shows a closer view of the "Detail A" region of FIG. 2. In the example of FIGS. 2-3, the elongate body also defines the inner working lumen 108, which, in this example, can include a nominal or preferred inner diameter of 0.07 inches (1.78 millimeters), and extends coaxially along a longitudinal axis of the elongate body from a distal end of the distal portion 202A to a proximal end of the proximal portion 202B. In the example of FIG. 2, an outer diameter of the elongate body can be in a range between 3.5 French (1.17 millimeters) and 8.0 French (2.67 millimeters), inclusive (e.g., such as an outer diameter of 6 French (2.0 mm)) at the distal portion 202A and can be the same or a slightly larger outer diameter (e.g., 6 French (2.0 millimeters) or slightly larger) at the proximal portion 202A of the sheath catheter 102. A working length of the sheath catheter 102, from its proximal end to its distal end, can be a length between 125 centimeters and 131 centimeters, inclusive, in an example.

The distal portion 202A of the sheath catheter 102 can include an inflatable distal balloon 204, such as can extend circumferentially around the elongate body of the distal portion 202A of the sheath catheter 102. The balloon 204 can be affixed to the elongate body of the distal portion 202A, such as at its proximal end by a proximal cuff 206A and at its distal end by a distal cuff 206B. In an example, these balloon cuffs 206A-B can be separated from each other by a working length of the balloon 204, such as a 10 millimeter working length. The cuffs 206A-B can be made from or augmented by including a metallic or other radiopaque material, such as can assist or enhance fluoroscopic or other radiographic viewing or observation; similarly, one or more other radiopaque markers can be provided at one or more other specified locations along a length of the sheath catheter 102, e.g., at a distal end tip of the sheath catheter 102.

When not inflated, the balloon 204 can be substantially flush with the outer diameter (e.g., 2 mm) of the distal portion 202A of the sheath catheter 102, but when inflated, the balloon 204 can expand to a larger outer diameter, such as about 6 millimeters in the example shown in FIG. 2. When inflated, the balloon 204 can stabilize the distal portion 202A of the sheath catheter 102, such as at a desired location within a cerebrovascular vessel, such as at an intracranial location beyond the petrous segment of the carotid artery. The balloon 204 can be made of a compliant material, such as polyurethane, such as to allow quick inflation and deflation, which can be helpful in reducing or minimizing procedure time, since its occlusion of the blood vessel when expanded may impede blood flow through the blood vessel during such time, thereby temporarily reducing blood perfusion to brain tissue regions otherwise perfused by the unoccluded blood vessel, to the extent that such blood vessel is not already completely occluded by a blood clot.

An annular or other dedicated inflation lumen 208 (e.g., which can be separate and distinct from the working lumen 108) can extend from a proximal inflation port at the proximal end or the proximal portion 202B of the sheath catheter 102 to a distal inflation port that opens into and allows fluid communication into an interior region of the balloon 204, such as via one or more inflation ports 300 (FIG. 3) at the proximal cuff 206A. In this way, saline, contrast agent, or another liquid fluid (e.g., a 50/50 or other mix of saline and liquid radiographic contrast agent) be pumped or otherwise introduced under positive pressure into the balloon 204, such as to inflate the balloon 204, such as from the proximal port location. One or more air purge vents or one-way valves can be provided, such as at the distal cuff 206B of the balloon 204, at the proximal cuff 206A of the balloon 204, or both, such as to allow air previously within the inflation lumen 207 or the balloon 204 to exit as the inflation fluid is introduced into the inflation lumen 208 at the proximal inflation port at the proximal end of sheath catheter 102.

Similarly, the balloon 204 can be deflated by the fluid exiting the proximal inflation port such as under negative pressure or passively. The inflation lumen 208 can include one or more fluid-communicative passages in the elongate body of the sheath catheter 102, such as a concentric ring cross-sectional passage coaxial to the working lumen 108 of the sheath catheter 102 and more distant from a longitudinal central axis of the sheath catheter 102.

The inflation lumen 208 can be located between an outer sheath 210 portion of the elongate body of the sheath catheter 102 and an inner sheath 212 portion of the elongate body of the sheath catheter 102. The outer sheath 210 can extend from a proximal end of the proximal portion 202B of the sheath catheter 102 to a proximal end of the balloon 204, e.g., extending to the proximal cuff 206A. The inner sheath 212 can extend from the proximal end of the proximal portion 202B of the sheath catheter 102 to a distal end of the distal portion of the sheath catheter 102. In an example, the outer sheath 210 can have an outer diameter of about 7 French (2.33 millimeters) and an inner diameter of about 0.089 inches (2.26 millimeters), and the inner sheath 212 can have an outer diameter of about 6 French (e.g., 2.0 millimeters) and an inner diameter of about 0.07 inches (1.78 millimeters).

In an example, the inner sheath 212, the outer sheath 210, or both, can include a polymer material (e.g., silicone or polyurethane) such as can be reinforced by a stiffener embedded therein, such as a metal or nylon braid or coil or a combination thereof. Variation in stiffness of the inner sheath 212, the outer sheath 210, or both, along the length of the sheath catheter 102 can be provided, for example, by varying a characteristic of the stiffener along the length of the sheath catheter 102, such as by varying an intercoil spacing between adjacent coils or an interbraid spacing between adjacent braids. This can be used to provide greater stiffness toward a proximal end or proximal portion 202B of the sheath catheter 102, such as relative to that at a more distal end or distal portion 202A of the sheath catheter 102, which can assist torqueing the intravascular instrument at or near its proximal end, while allowing its distal end more flexibility, such as can be needed to twist through tortuous blood vessels, such as particularly small and tortuous at cerebrovascular intracranial locations beyond the petrous segment of the carotid artery. A variable stiffness or durometer of the outer sheath 210 can similarly be provided, such as by using different materials or structures in different zones along the length of the sheath catheter 102.

An atraumatic distal segment can be included, distal to the balloon 204. In an example, this distal segment can be between 4 millimeters and 10 millimeters in length, with a soft distal tip, and having an outer diameter of about 6 French (2.0 millimeters).

In an example, the stiffness of the sheath catheter, including that of its working lumen 108 extending from its proximal end to and through the atraumatic distal segment, is specified such as to be sufficient to be capable of permitting an aspiration-based thrombectomy by applying suction (e.g., up to 300 psi) via the working lumen 108, such as by using A Direct Aspiration first Pass Technique (ADAPT) without distorting or bursting. This can include building up suction using an external vacuum/suction pump, such as with a valve between the external vacuum pump and the working lumen 108 being closed to allow suction to build up. Then, the valve can be opened, such as to create a sudden suction within the working lumen 108. Such sudden suction can permit a blood clot located within the blood vessel and distal to the distal opening of the working lumen to be sucked into (or corked against) against the distal opening of the working lumen 108. The blood clot can be removed by aspirating it through the working lumen 108 and out a proximal end of the working lumen 108 or the blood clot can be removed by withdrawing the sheath catheter 102 from the vasculature with the blood clot located in the working lumen 108 or corked against a distal opening of the working lumen 108, such as with suction still being applied during withdrawal of the sheath catheter 102 from the vasculature.

A biocompatible hydrophilic or lubricious material or coating can be provided on the outer sheath 210, such as along its entire length, or a specified portion (e.g., distal portion) thereof, such as to help such portion of the sheath catheter 102 more easily slide to a desired location within the vasculature. Similarly, the inner working lumen 108 of the sheath catheter can be made lubricious, such as by appropriate selection or coating of the material of the inner sheath 212, such as by providing a Teflon® or other polytetrafluoroethylene or other liner on the interior of the inner sheath 212 along the wall of the working lumen 108 along all or a specified portion of its length. This can help make it easier for the angioscope 104, the cerebrovascular pathology treatment catheter 106, or one or more other instruments to be introduced into and slid within the working lumen 108 of the sheath catheter 102.

FIG. 4 is a schematic illustrating an example of portions of the angioscope 104. In the example of FIG. 4, the angioscope 104 can include a forward-viewing fiberoptic angioscope 104. The angioscope 104 can include one or more fibers 402 such as in an annular bundle that can concentrically surround a Coherent Fiber Bundle (CFB) of imaging optical fibers 404 that can be centrally located along a longitudinal axis of the angioscope 104, such as behind a GRIN or other lens 406 located at a distal end of the angioscope 104. A polymeric jacket 405 can concentrically surround and encapsulate the imaging optical fibers 404 and the lens 406, such as with the jacket 405 being concentrically located between the imaging optical fibers 404 and the illumination fibers 402. The illumination fibers 402 can be configured to communicate light from an external light source, which can be optically coupled to a proximal end of the angioscope 104, to a distal end of the angioscope 104. The distally-projected light can be used to forwardly illuminate into the vasculature into which a distal end of the angioscope 104 has been inserted, or to forwardly illuminate within the working lumen 108 of the sheath catheter 102, or both, such as to enhance viewing using the imaging optical fibers 404.

The coherent fiber bundle of imaging optical fibers 404 can extend between proximal and distal portion of the angioscope 104, such that the angioscope can have a working length of about 160 centimeters, in an example. In an example, individual ones of the imaging fibers 404 can have an outer diameter of about 2.5 micrometers. The group of imaging fibers 404 can include, for example, 3000 imaging fibers, each providing a proximally-viewable "pixel" of the distally forward-looking imaging fibers 404 at a proximal end of the angioscope. The imaging fibers 404 can include a common cladding such as can be located or shared between individual ones of the imaging fibers 404. The illumination fibers 402 can include an uncladded arrangement of illumination fibers 404, such as can be concentrically arranged annularly around the imaging fibers 404. In an example, individual ones of the illumination fibers 404 can have an outer diameter between 25 micrometers and 50 micrometers. In an example, the GRIN or other lens 406 can the lens have a diameter of 250 micrometers or less and an axial length of 500 micrometers +/− 100 micrometers.

The GRIN or other lens 406 can include or be coated with an optically transparent (e.g., at the illumination and imaging wavelengths of the angioscope 104) clot-resistant or anti-clot material, such as for example a heparin-based coating. A silicone, polyurethane, or other polymeric (e.g., Pebax® elastomer) outer sheath 408 can circumferentially surround an optics lumen (e.g., about 0.0165 inches (4.19 millimeters) in diameter) carrying the illumination fibers 404, the lens 406, and the imaging fibers 404. Such outer sheath 408 can provide an interior lumen that can optionally be coated with a hydrophilic or lubricious material, such as Teflon® or the like, such as to permit easier insertion of optical components into such interior lumen. The outer sheath 408 can include different materials in different longitudinal zones, such as to provide more flexibility in one or more distal regions (e.g., using 35D Pebax® elastomer material in such a distal zone) than in one or more proximal regions (e.g., using 45D to 55D Pebax® elastomer material in such a proximal zone, e.g., of proximal zone length of about 75 centimeters) or in one or more intermediate regions (e.g., using 45D Pebax® elastomer material in such an intermediate zone).

The outer sheath 408 can optionally include an embedded microcoil stiffener structure to prove additionally rigidity, such as can include a coil pitch that increases between coils toward a distal direction of the angioscope 104. This can help provide more flexibility toward a distal portion of the angioscope 104 than at a more proximal region, at which more rigidity, pushability, trackability, and kink-resistance can be provided. The stiffening coil can be omitted entirely at a most distal portion of the angioscope 104, such as to leave a most-distal end zone of a length between about 10 millimeters and 30 millimeters that is softer and more flexible and more atraumatic, which is helpful in treating cerebrovascular pathologies at deep and tortuous vascular locations within the subject's skull, including beyond the petrous segment of the carotid artery, In the example of FIG. 4, the outer diameter of the angioscope 104 can be about 1.7 French (567 micrometers) in diameter at its soft and atraumatic distal end and about 2.4 French (800 micrometers) at the proximal end of the angioscope 104. The forward-viewing fiberoptic angioscope shown in FIG. 4 can be sized and shaped to be inserted from a proximal portion of the sheath catheter 102 into the working lumen 108 of the sheath catheter 102 such as to allow a distal portion of the angioscope 104 to (optionally) extend beyond a distal opening of the working lumen 108 of the sheath catheter 102 such as to be capable of permitting forwardly viewing and inspecting a cerebrovascular pathology using the angioscope 104.

FIGS. 5A, 5B, 5C, 5D, 5E, 5F, 5G, and 5I illustrate an example of a method of using one or more portions of the system 100 for a stent retriever thrombectomy under viewing by the angioscope 104, such as to help provide better results than would otherwise be the case if the stent retriever thrombectomy were to be performed under fluoroscopy alone, without the benefit or added benefit of enabling concurrent forward-looking intravascular viewing using the angioscope 104.

Figure 5A:
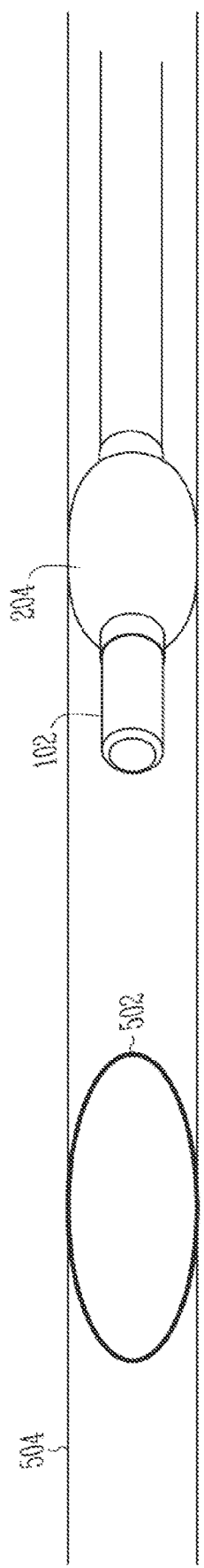

In the example of FIG. 5A, a distal end of the sheath catheter 102 is introduced into the vasculature and advanced toward but just short of a cerebrovascular pathology (e.g., thrombus 502) at an intracranial location within an artery 504, such as beyond a petrous segment of the carotid artery. External fluoroscopic radiologic guidance can be used to guide such introduction of the sheath catheter 102. which can include one or more radiographically viewable markers. A guidewire can optionally be first inserted into the artery 504, and the sheath catheter 102 can be inserted over-the-wire, such as with the guidewire located within the working lumen 108 of the sheath catheter 102 during its introduction into the artery 504 and steering toward the thrombus 502. The balloon 204 can then be inflated, such as to stabilize a distal portion of the sheath catheter 102 at a desired location within the artery 504, e.g., just short of the thrombus 502. The guidewire, if any, can then be withdrawn via a proximal opening of the working lumen 108 of the sheath catheter 102.

Figure 5B:
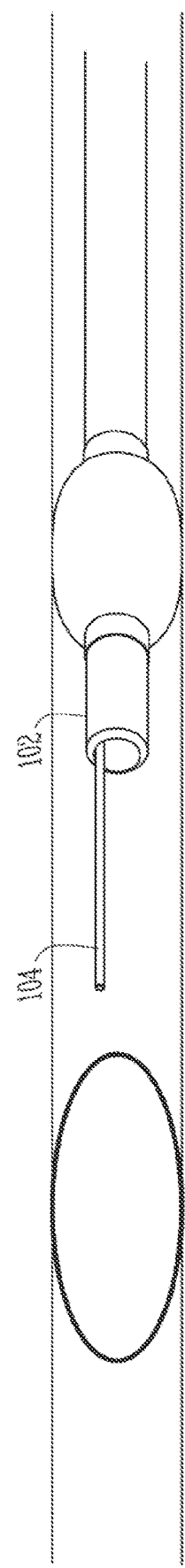
Figure 5A:
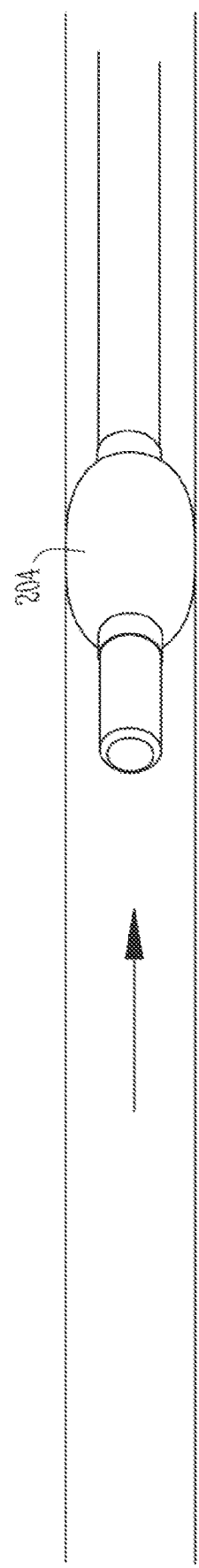
Figure 5B:
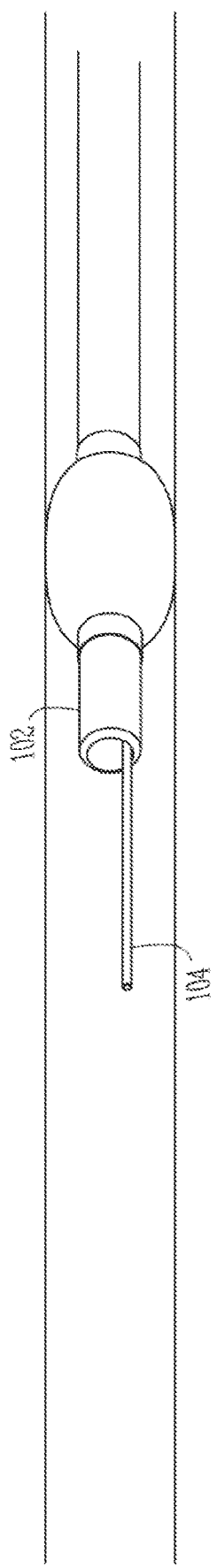

FIG. 5B shows an example of a following or subsequent step in which a distal end of the angioscope 104 can be inserted into a proximal opening of the working lumen 108 of the sheath catheter 102, and advanced toward the thrombus 502, such as by pushing on a proximal portion of the angioscope 104. The distal end of the angioscope 104 can optionally be advanced beyond a distal opening of the working lumen 108 of the sheath catheter 102 for forward-viewing of the thrombus 502 or, alternatively, such forward viewing of the thrombus 502 can optionally be carried out with the distal end of the angioscope 104 remaining slightly retracted within the working lumen 108 of the sheath catheter 102. Intravascular viewing of the thrombus 502 can be assisted by gently introducing a clear saline flush through the working lumen of the sheath catheter 102 into the vasculature beyond the inflated balloon 204. This can allow a gentle flushing of more visually opaque red blood cells away from a region between the distal end of the angioscope 104 and the thrombus 502, allowing a clearer visual assessment of the thrombus 502 using the angioscope 104.

Intravascular visual assessment of the thrombus 502 can be used to provide guidance for planning the method of treatment. The visualized color of the thrombus 502 can provide an indication of its composition, which can be used to decide whether to stent and leave the thrombus 502 within the vasculature, or to use a retriever stent or other technique to remove the thrombus 502 from the vasculature.

FIG. 5C shows an example of a following or subsequent step in which a guidewire 506 can be inserted via a proximal opening of the working lumen 108 of the sheath catheter 102. A distal end of the guidewire 506 can be advanced through the working lumen 108 of the sheath catheter 102 and out a distal opening of the working lumen 108 of the sheath catheter 102 and toward, into, or all the way through the thrombus 502. During this step, a portion of the angioscope 104 can remain within the working lumen 108 of the sheath catheter 102, such as to allow concurrent viewing of the guidewire 506 insertion, such as from a location within the working lumen 108 of the sheath catheter 102 or from a location beyond a distal opening of the working lumen 108 of the sheath catheter 102.

FIG. 5D shows an example of a following or subsequent step in which a cerebrovascular pathology treatment catheter, such as a stent retriever catheter 508 can be inserted via a proximal opening of the working lumen 108 of the sheath catheter 102. A distal portion of the stent retriever catheter 508 can be advanced over the guidewire 506, such as toward, into, or all the way through the thrombus 502. At least a distal portion of the stent retriever catheter 508 can be retractable or can include a retractable sheath, such as can be retracted from an external location via a proximal portion of the stent retriever catheter 508, to deploy a self-expanding stent retriever 510 or other similar thrombus engagement and retrieval device, such as after withdrawing the guidewire 506 from the stent retriever catheter 508 and replacing the withdrawn guidewire 506 with the stent retriever 510 inserted into the stent retriever catheter 508. The angioscope 104 can be left in place, such as with its distal portion located just short of the thrombus 502 to permit viewing of the thrombus during this portion of the procedure.

FIG. 5E shows an example of a following or subsequent step in which the guidewire 506 can be retracted through and out of the working lumen 108 of the sheath catheter 102. The stent retriever 510 can then be inserted, such as via a working lumen of the stent retriever catheter 508. The stent portion of the stent retriever 510 can then be allowed to self-expand outward into engagement with the thrombus 502. The expanded stent retriever 510 can be left expanded for a period of time (e.g., 5 minutes) to set into the thrombus 502. The angioscope 104 can be left in place, such as with its distal portion located just short of the thrombus 502 to permit viewing of the thrombus during this portion of the procedure. The stent retriever catheter 508 and the stent retriever 510 can then be retracted, such as with the expanded stent portion of the stent retriever 510 still in place engaging the snared thrombus 502. The angioscope 104 can also be left in place, such as with its distal portion located just short of the thrombus 502 to permit viewing of the thrombus during this portion of the procedure.

FIG. 5F shows an example of a following of subsequent step in which the stent retriever catheter 508 and its distal stent retriever 510 can be retracted through and out of the working lumen 108 of the sheath catheter 102, together with the snared thrombus 502. Concurrently or prior to this, the angioscope 104 can also be retracted through and out of the working lumen 108 of the sheath catheter 102, such as while permitting viewing of the snared thrombus 502 as it is being extracted through the working lumen 108 of the sheath catheter.

FIG. 5G shows an example of a following or subsequent step in which the angioscope 104 can optionally again be inserted into a proximal opening of the working lumen 108 of the sheath catheter 102. A distal portion of the angioscope can optionally again be advanced toward or beyond the distal opening of the working lumen 108 of the sheath catheter 102, such as to permit intravascular viewing of the cleared blood vessel from within or beyond the working lumen 108 of the sheath catheter 102. Such viewing can help a physician determine whether any remnants of the thrombus remain or whether any more distal emboli or other cerebrovascular pathologies can be observed, which, in turn, can help determine treatment efficacy or any need or strategy for further treatment. Such further treatment can include repeating the process of retrieving a thrombus using a stent retriever, such as described herein, or using aspiration or another treatment technique, such as for such further treatment. In an experimental animal model study, such post-treatment inspection by the angioscope 104 did reveal embolic remnants, which, in turn were then intravascularly retrieved via the working lumen 108 of the sheath catheter 102.

FIG. 5H shows an example of a following or subsequent step in which, if the vessel is clear, the angioscope 104 can be retracted and removed from the body via the working lumen 108 of the sheath catheter 102. Then, the balloon 204 can be deflated, such as via the inflation lumen 208 of the sheath catheter 102. If the clot 502 or a portion thereof remains, further treatment can be applied, such as explained herein with respect to FIG. 5G and elsewhere.

Figure 5I:
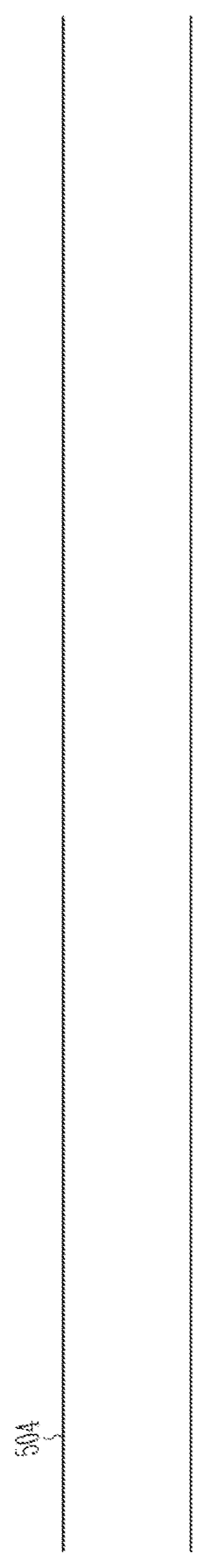

FIG. 5I shows an example of a desirable result, e.g., reperfusion is achieved through the cleared artery, such as after the various treatment devices have been removed from the blood vessel lumen. As described herein, performing one or more steps of such procedure while allowing intravascular viewing by the angioscope 104, e.g., in addition to radiographic fluoroscopic viewing, can help improve treatment efficacy, reduce treatment time, or both. It can also help reduce or eliminate the time needed for radiographic fluoroscopic viewing, thereby reducing or minimizing radiation dose exposure to the patient, to the operator, or both. In particular, the real-time intravascular viewing capability when using the angioscope 104 allows the user to make real-time adjustments in the therapy being provided. For example, if the user observes that the stent retriever 510 and its engaged dot 502 being retrieved are moving at different speeds as the stent retriever catheter 508 is being withdrawn toward or into the working lumen 108 of the sheath catheter 102, as viewed intravascularly via the angioscope 104. then the user can infer that the stent retriever 510 is losing its grip of the clot 502 being retrieved, and the user can react to such visual information feedback by pulling more gently on the proximal end of the stent retriever catheter 508, or by letting the clot 502 "set" into engagement with the stent retriever 510 for a little longer before resuming pulling on the proximal end of the stent retry ever catheter 508, or otherwise manipulating or adjusting the stent retriever 510 to gain better engagement of the clot 502 being pulled toward or into the working lumen 108 of the sheath catheter 102 by the stent retriever 510. Such real-time visual feedback from the angioscope 104 can help improve the efficacy of such a critical clot-removal procedure.

FIGS. 6A, 6B, 6C, 6D, 6E, 6F, and 6G illustrate an example of a method of using one or more portions of the system 100 for an aspiration-based thrombectomy under viewing by the angioscope 104, such as to help provide better results than would otherwise be the case if the aspiration-based thrombectomy were to be performed under fluoroscopy alone, without the benefit or added benefit of enabling concurrent forward-looking intravascular viewing using the angioscope 104.

Figure 6A:
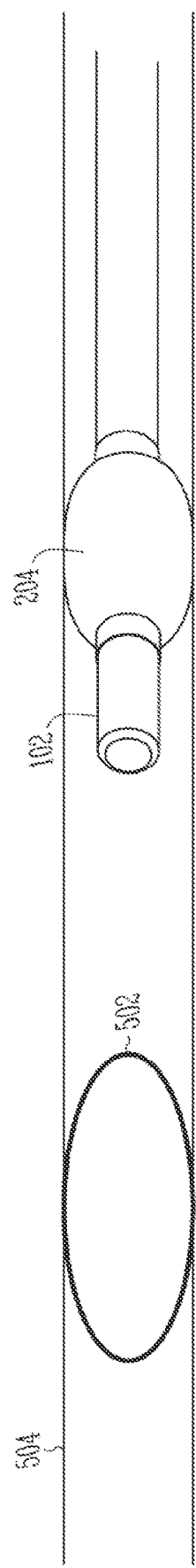

In the example of FIG. 6A, a distal end of the sheath catheter 102 is introduced into the vasculature and advanced toward but just short of a cerebrovascular pathology (e.g., thrombus 502) at an intracranial location within an artery 504, such as beyond a petrous segment of the carotid artery. External fluoroscopic radiologic guidance can be used to guide such introduction of the sheath catheter 102, which can include one or more radiographically viewable markers. A guidewire can optionally be first inserted into the artery 504, and the sheath catheter 102 can be inserted over-the-wire, such as with the guidewire located within the working lumen 108 of the sheath catheter 102 during its introduction into the artery 504 and steering toward the thrombus 502. The balloon 204 can then be inflated, such as to stabilize a distal portion of the sheath catheter 102 at a desired location within the artery 504, e.g., just short of the thrombus 502. The guidewire, if any, can then be withdrawn via a proximal opening of the working lumen 108 of the sheath catheter 102.

Figure 6B:
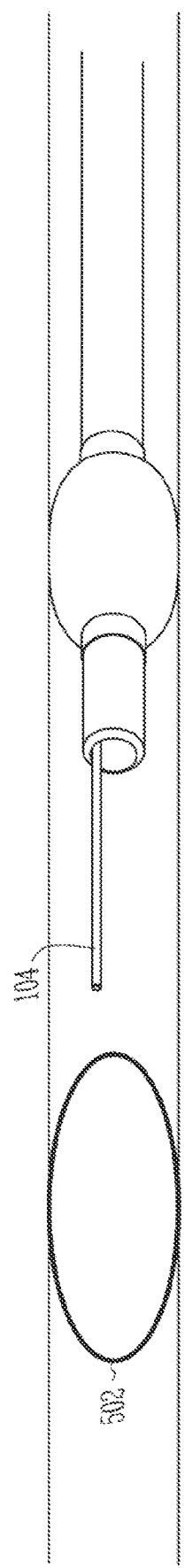

FIG. 6B shows an example of a following or subsequent step in which a distal end of the angioscope 104 can be inserted into a proximal opening of the working lumen 108 of the sheath catheter 102, and advanced toward the thrombus 502, such as by pushing on a proximal portion of the angioscope 104. The distal end of the angioscope 104 can optionally be advanced beyond a distal opening of the working lumen 108 of the sheath catheter 102 for forward-viewing of the thrombus 502 or, alternatively, such forward viewing of the thrombus 502 can optionally be carried out with the distal end of the angioscope 104 remaining slightly retracted within the working lumen 108 of the sheath catheter 102. Intravascular viewing of the thrombus 502 can be assisted by gently introducing a clear saline flush through the working lumen of the sheath catheter 102 into the vasculature beyond the inflated balloon 204. This can allow a gentle flushing of more visually opaque red blood cells away from a region between the distal end of the angioscope 104 and the thrombus 502, allowing a clearer visual assessment of the thrombus 502 using the angioscope 104.

Intravascular visual assessment of the thrombus 502 can be used to provide guidance for planning the method of treatment. The visualized color of the thrombus 502 can provide an indication of its composition, which can be used to decide whether to stent and leave the thrombus 502 within the vasculature, or to use a retriever stent or other technique to remove the thrombus 502 from the vasculature.

Figure 6C:
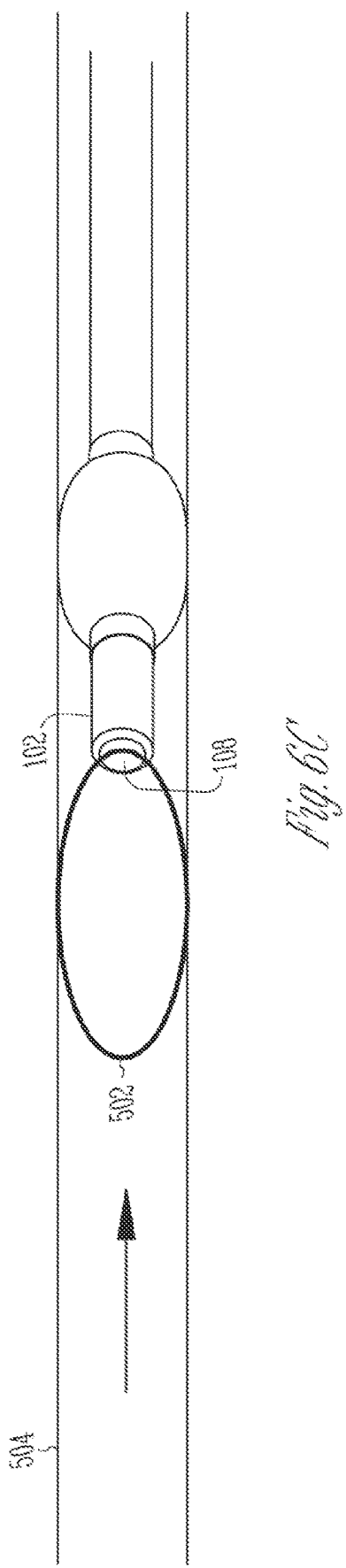

FIG. 6C shows an example of a following or subsequent step in which the angioscope 104 has been retracted slightly such that its distal end is located within the working lumen 108 of the sheath catheter 102. Then, a proximal end of the working lumen 108 of the sheath catheter can be connected to an external aspiration suction source, such as a vacuum pump, such as via a two-way or a three-way or other valve, or another aspiration suction source, such as a syringe having a plunger that can be retracted to create a vacuum. The valve can initially be kept closed when the suction pump or other suction source is turned on or otherwise actuated, such as to isolate the working lumen 108 from suction being built up by the suction pump on the other side of the valve. When it is determined, by the operator or otherwise, that sufficient suction has been built up, the valve can be rapidly opened, such as to apply suction to the working lumen 108 of the sheath catheter, and thereby draw the thrombus 502 toward, against, or into the working lumen 108 of the sheath catheter 102.

Having a larger inner diameter of the working lumen 108 can facilitate extremely quick ingestion of a blood clot, especially if the blood clot is smaller than the inner diameter of the working lumen 108. When combined with a jerk technique (e.g., allowing the vacuum pump or other suction source to build up pressure before flipping an actuation switch to open a valve to apply vacuum to the working lumen 108) it creates a hoovering effect. Adding the balloon 204 focuses the entire pressure onto the clot rather than merely applying suction to the blood near to the distal tip of the catheter 102 flowing towards the clot and then into the working lumen 108 of the catheter 102. These factors can combine to help create balloon hoovering, which can help provide optimal conditions for fully ingesting a clot rather than achieving corkscrewing of the clot, which, in turn, is much safer for the patient. The focused pressure pulls blood from distal regions rather than proximal regions which can help inhibit or prevent emboli from flowing distally.

By viewing concurrently in real-time with the slightly retracted angioscope 104. the user can observe whether the thrombus 502, the user can see whether the thrombus 502 has been ingested under suction (e.g., provided by the suction pump, syringe, or other suction source) into the working lumen 108 of the sheath catheter 102 or has instead merely been sucked and "corked" against the distal end of the working lumen 108 of the sheath catheter 102. In the latter case, suction can be maintained (e.g., using the pump, syringe, or other suction source) in the working lumen 108 of the sheath catheter to maintain the thrombus corked against the distal end of the working lumen 108 of the sheath catheter 102. The balloon 204 can be deflated under suction and the sheath catheter 102 and the angioscope 104 can be withdrawn together, along with the corked thrombus 502, while maintaining suction in the working lumen 108 of the sheath catheter 102 (e.g., using the pump, syringe, or other suction source) to hold the corked thrombus 502 against the distal end of the working lumen 108 of the sheath catheter 102.

Figure 6D:
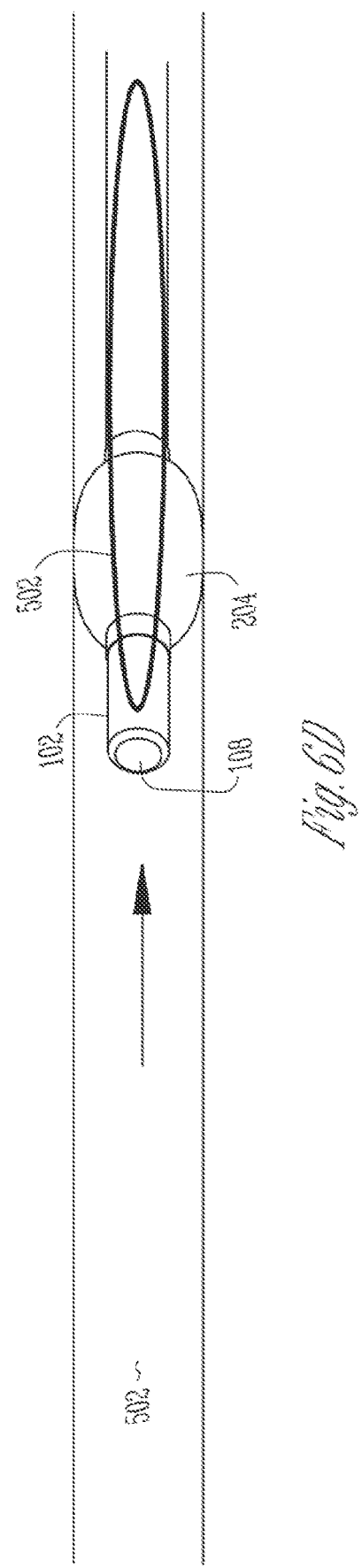

FIG. 6D shows an example of a following or subsequent step for the case in which the thrombus 502 has been ingested into the working lumen 108 of the sheath catheter 102, such as can be viewed intravascularly in real-time by observing via the angioscope 104. In some instances, it may be possible to use the angioscope 104 to watch the thrombus 502 be ingested into the working lumen 108 of the sheath catheter 102, and to watch the thrombus 502 be sucked past the angioscope to a more proximal location within the working lumen 108 of the sheath catheter 102.

FIG. 6E shows an example of a following or subsequent step in which the thrombus 502 has been completely removed from the body and from the working lumen 108 of the sheath catheter 102, and the aspiration pump has been disconnected from the working lumen 108 of the sheath catheter. As shown in the example of FIG. 6E, the angioscope 104 can be used for viewing the vessel location, such as to inspect for thrombus remnants or distal emboli. This can include extending the distal tip of the angioscope beyond the distal opening of the working lumen 108 of the sheath catheter 102, if desired. Clear saline flush can be delivered via the working lumen 108 of the sheath catheter 102, if desired, to help improve visual observation by flushing away red blood cells from the field of view of the angioscope 108.

FIG. 6F shows an example of a following or subsequent step in which the vessel has been cleared. (If the clot remains or other emboli are observed, the aspiration or another thrombectomy procedure can be repeated). The angioscope 108 can then be removed from the body via the working lumen 108 of the sheath catheter 102, such as by pulling on a proximal end of the angioscope 104 to retract it. The balloon 204 can then be deflated. The sheath catheter 102 can then be removed from the body, such as by pulling on a proximal end of the sheath catheter 102 to retract it.

Figure 6G:
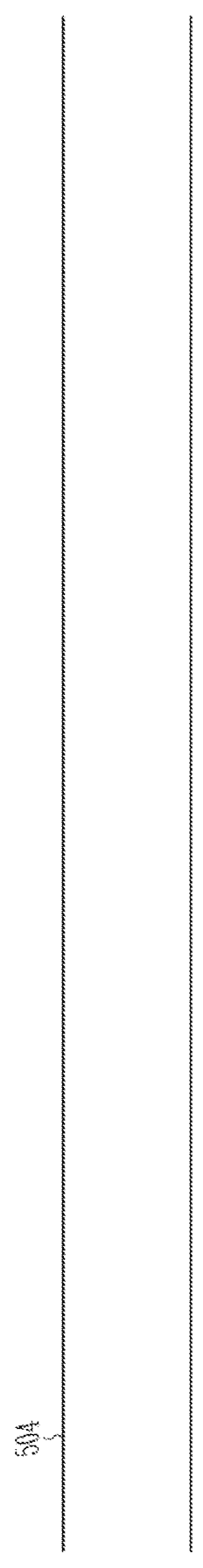

FIG. 6G shows an example of a desirable result, e.g., reperfusion is achieved through the cleared artery, such as after the various treatment devices have been removed from the blood vessel lumen. As described herein, performing one or more steps of such procedure while allowing intravascular viewing by the angioscope 104, e.g., in addition to radiographic fluoroscopic viewing, can help improve treatment efficacy, reduce treatment time, or both. It can also help reduce or eliminate the time needed for radiographic fluoroscopic viewing, thereby reducing or minimizing radiation dose exposure to the patient, to the operator, or both.

Although FIGS. 6A-6G has emphasized an aspiration-based thrombectomy procedure via a working lumen 108 of the sheath catheter 104, such aspiration-based techniques can be combined with the stent retriever thrombectomy techniques such as described with respect to FIGS. 5A-5I, or a separate aspiration catheter can be inserted via the working lumen 108 of the sheath catheter 104 (similar to insertion of the stent retriever as described with respect to FIGS. 5A-5I) and the thrombus can be aspirated via a working lumen of such separate aspiration catheter.

FIG. 7 shows an example of portions of a cerebrovascular or other intravascular pathology treatment kit or system 100, similar to that shown in FIG. 1, but including an optional cerebrovascular or other intravascular pathology treatment catheter 106 that, in the example of FIG. 7, can include a thrombolytic occlusion device, such as coil deployment catheter 710, such as can be used for treating an aneurysm such as by deploying aneurysm coils to promote thrombosis and occlusion within an aneurysm.

FIGS. 8A, SB, 8C, 8D, 8E, and 8F illustrate an example of a method of using one or more portions of the system 100 for aneurysm treatment via occlusion, under viewing by the angioscope 104, such as to help provide better results than would otherwise be the case if the aneurysm occlusion treatment were to be performed under fluoroscopy alone, without the benefit or added benefit of enabling concurrent forward-looking intravascular viewing using the angioscope 104.

In the example of FIG. 8A, a distal end of the sheath catheter 102 is introduced into the vasculature and advanced toward but just short of a cerebrovascular pathology (e.g., basilar tip or other aneurysm 802) at an intracranial location within an artery 804, such as beyond a petrous segment of the carotid artery. External fluoroscopic radiologic guidance can be used to guide such introduction of the sheath catheter 102, which can include one or more radiographically viewable markers. A guidewire can optionally be first inserted into the artery 504, and the sheath catheter 102 can be inserted over-the-wire, such as with the guidewire located within the working lumen 108 of the sheath catheter 102 during its introduction into the artery 504 and steering toward the aneurysm 802. The balloon 204 can then be inflated, such as to stabilize a distal portion of the sheath catheter 102 at a desired location within the artery 804, e.g., just short of the aneurysm 802. The guidewire, if any, can then be withdrawn via a proximal opening of the working lumen 108 of the sheath catheter 102.

Figure 8B:
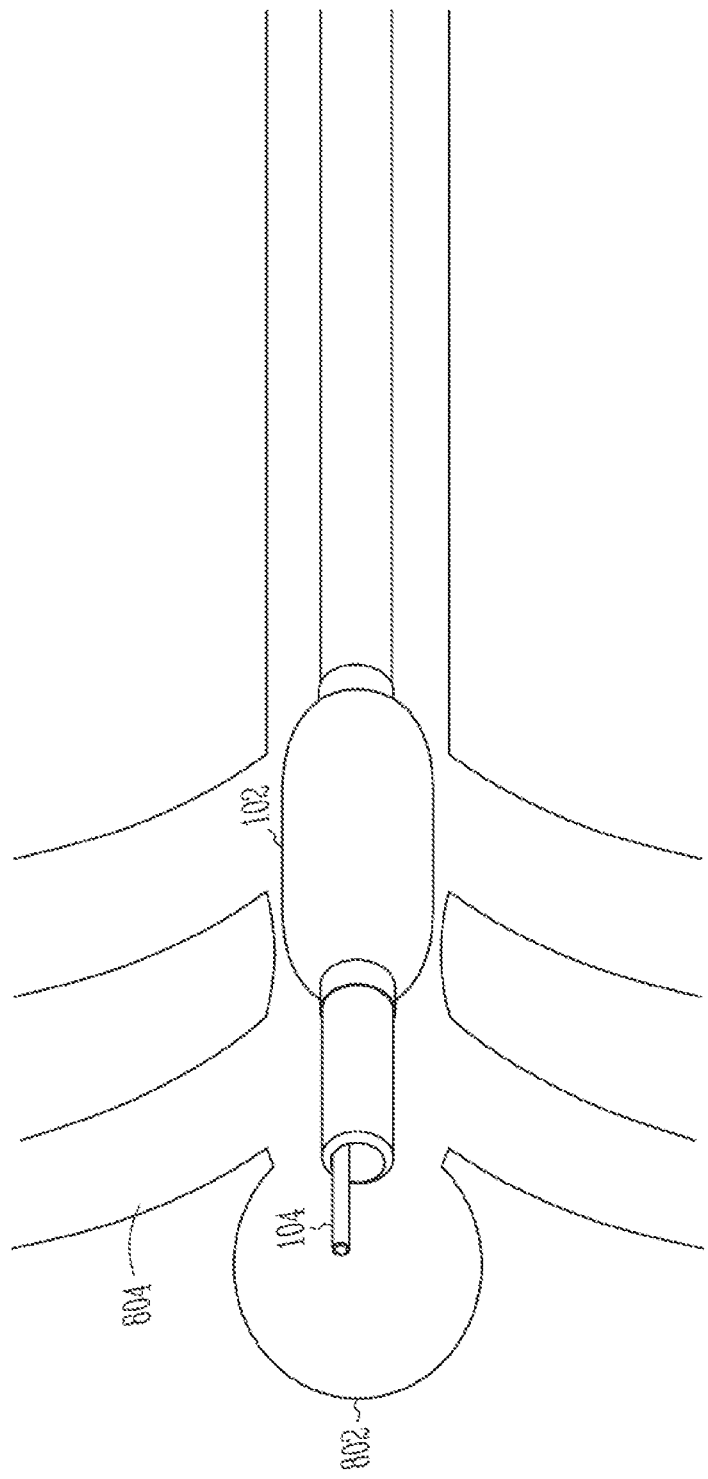
Figure 9D:
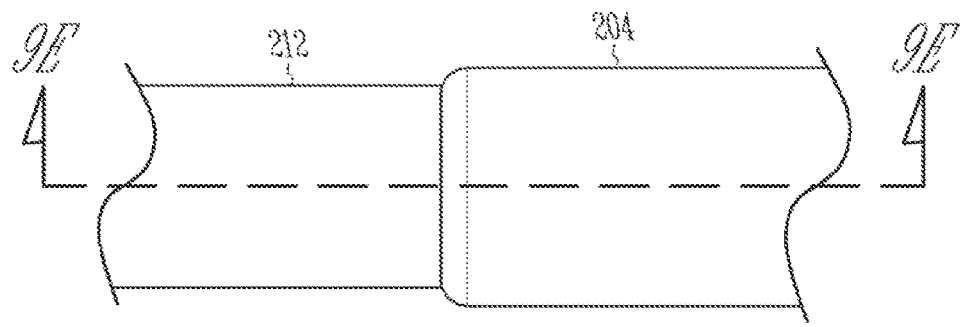
Figure 9E:
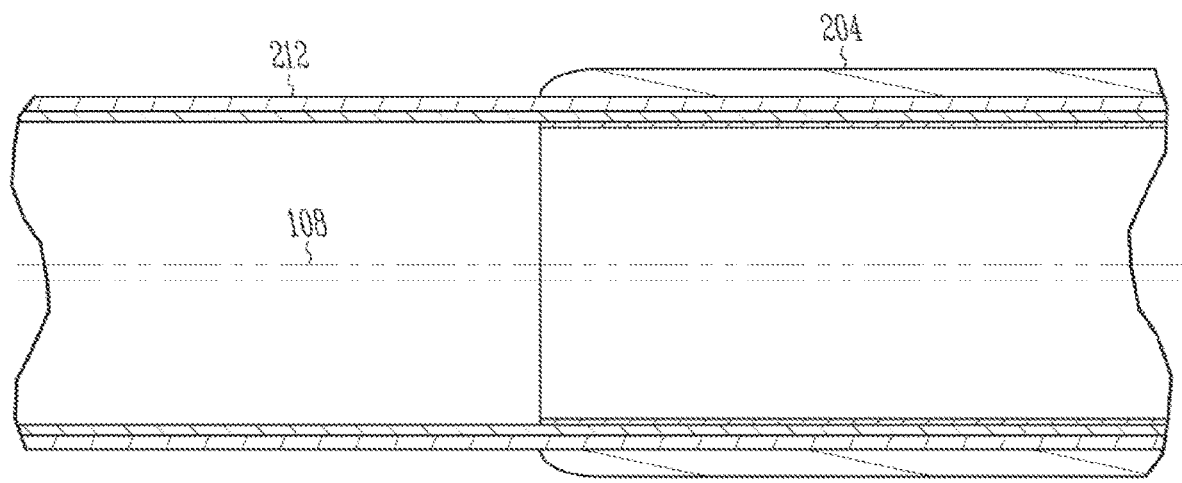
Figure 9F:
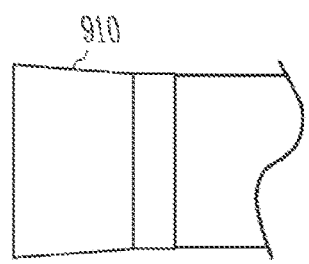

FIG. 8B shows an example of a following or subsequent step in which a distal end of the angioscope 104 can be inserted into a proximal opening of the working lumen 108 of the sheath catheter 102, and advanced toward the aneurysm 802, such as by pushing on a proximal portion of the angioscope 104. The distal end of the angioscope 104 can optionally be advanced beyond a distal opening of the working lumen 108 of the sheath catheter 102 such as for forward-viewing of the aneurysm 802 or, alternatively, such forward viewing of the aneurysm 802 can optionally be carried out with the distal end of the angioscope 104 remaining slightly retracted within the working lumen 108 of the sheath catheter 102. Intravascular viewing of the aneurysm 802 can be assisted by gently introducing a clear saline flush through the working lumen of the sheath catheter 102 into the vasculature beyond the inflated balloon 204. This can allow a gentle flushing of more visually opaque red blood cells away from a region between the distal end of the angioscope 104 and the aneurysm 802, allowing a clearer visual assessment of the aneurysm 802 using the angioscope 104.

Intravascular visual assessment of the aneurysm 802 can be used to provide guidance for planning the method of treatment. The visualized color or other characteristic of the aneurysm 802 can help decide how best to reinforce the aneurysm 802 to help avoid its rupture, for example, whether to insert aneurysm coils or a liquid embolic agent or both to treat the aneurysm 802.

FIG. 8C shows an example of a following or subsequent step in which a cerebrovascular pathology treatment catheter 110, such as an aneurysm coil deployment catheter 710 can be inserted via a proximal opening of the working lumen 108 of the sheath catheter 102. A distal portion of the coil deployment catheter 710 can be advanced (e.g., over a guidewire or otherwise, such as toward or into the aneurysm 802. At least a distal portion of the coil deployment catheter 108 can dispense one or more aneurysm coils, such as to occlude the aneurysm 802 and promote thrombosis therewithin to boost its structural integrity and help avoid its rupture. The angioscope 104 can be left in place, such as with its distal portion located just short of or extending into the aneurysm 802 to permit viewing of the aneurysm 802 during this portion of the procedure.

FIG. 8D shows an example of a following or subsequent step in which a cerebrovascular pathology treatment catheter 110, such as a coil deployment catheter 710 can be used to inject a thrombolytic agent or structure (such as one or more aneurysm coils, e.g., coil pack 808) such as can be inserted via a working lumen of the coil deployment catheter 710. The angioscope 104 can be left in place, such as with its distal portion located within or just short of the aneurysm 802 such as to permit viewing of aneurysm 802 during this portion of the procedure. In this way, the user can be provided real-time visualization information that can help the user determine whether or when the coil infusion into the aneurysm 802 is sufficient, whether the coil packing is distributed as desired within the aneurysm 802, or the like.

FIG. 8E shows an example of a following or subsequent step in which a cerebrovascular pathology treatment catheter 110, such as a coil deployment catheter 710 can be removed, while the angioscope 802 can optionally be temporarily left in place, such as to allow the user to optionally visually assess the treated aneurysm 802 or one or more nearby intravascular anatomical regions of interest. Such post-treatment intravascular visualization can be used to help determine whether the aneurysm 802 has been properly packed with coils 808 such that no coils 808 protrude outward from the aneurysm 802 into the main vessel, which could increase a risk of clotting and thrombus formation in the main vessel. If a coil 808 does so protrude into the main vessel, a distal end of the angioscope 104 can optionally be used to push such a protruding portion of the coil 808 back into the aneurysm 802 such as to help reduce or avoid such risk.

FIG. 8F shows an example of a following or subsequent step in which the balloon 204 can be deflated and the sheath catheter 102 and angioscope 104 can be removed together by retracting or pulling on a proximal portion of these instruments. Alternatively, the angioscope 104 can be removed first, then the balloon 204 can be deflated and the sheath catheter 102 can be removed.

The angioscope 104, such as described above with respect to FIG. 4, including its small distal diameter dimension and the selected materials and their rigidity or other characteristics, can provide a bend radius at a distal portion of the angioscope 104 of less than or equal to 5 millimeters, which is beyond the capabilities of an coronary or peripheral angioscope, which would have a bend radius of 25 millimeters or more, due to its use of a thicker or stiffer polyamide sheath. By providing an angioscope 104 with a bend radius of 5 millimeters or less, access to the middle cerebral artery (MCA) or other tortuous intercranial locations beyond a petrous segment of the coronary artery using the angioscope 104 are possible, such as for carrying out the thrombus removal, aneurysm treatment, or other cerebrovascular pathology treatment techniques described herein. By contrast, by using Pebax® or similar sheathing material for the outer sheath 408 of the angioscope 104, as well as a reinforcing coil or braid at one or more specified locations along a length of the angioscope 104, the present angioscope 104 can be configured to provide sufficient distal flexibility and proximal rigidity with a small-enough diameter and bend radius to enable use in the middle cerebral artery (MCA) or at another intercranial location beyond a petrous segment of the coronary artery, including at very tortuous cerebrovascular locations and within tiny cerebrovascular pathologies, such as within a basilar tip or other aneurysm, as explained herein.

In the example described above with respect to FIG. 4, distal flexibility and steerability of the angioscope 104 may be limited primarily by the stiffness associated with the GRIN or other lens 406, but such lens need only have an axial length of about 0.5 millimeters. By contrast, other imaging approaches, such as Scanning Fiber Endoscopy (SFE), IntraVascular Ultrasound (IVUS), Optical Coherence Tomography (OCT) and Complementary Metal Oxide Semiconductor (CMOS) imaging require a longer stiff section, limiting the usefulness of such techniques for cerebrovascular diagnosis or treatment, such as at an intracranial location beyond the petrous segment of the carotid artery. For example, an SFE approach was reported to involve a stiff section longer than 1.5 millimeters, which would be difficult to bend around cerebrovascular intravascular regions such as the ophthalmic arch (C6) or the bend from the petrous segment (C2). CMOS. IVUS, and OCT generally have longer than 1 mm stiff segments, which would encounter difficulty in making it around the opthalmic arch (C6). By contrast, in the example of the present approach such as described with respect to FIG. 4, using an angioscope 104 having only a 0.5 mm long stiff segment allows a distal portion of the angioscope 104 to safely travel through all these cerebrovascular segments without damage to the patient. This is very useful for enabling cerebrovascular diagnosis and imaging, with such constraints extending beyond constraints imposed in intravascularly diagnosing or imaging other parts of the human body.

Furthermore, peripheral or coronary angioscopes generally have an outer diameter between 5 French (1.67 millimeters) and 7 French (2.33 millimeters), which is too large for use in many neural vessels in which thrombus removal, aneurysm treatment, or other cerebrovascular pathology interventional treatments are desired. Existing angioscopes also have very limited resolution, limiting their usefulness in the present intracranial applications, in which providing real-time full-color visualization of cerebrovascular pathologies is needed, such as to intravascularly assess in real-time the characteristics or composition of the cerebrovascular pathology or its treatment, so as to be able to alter or adjust the treatment such as to help improve its efficacy. By contrast, the present angioscope 104 can be configured with an imaging fiber bundle, lens, and other features that can provide a very small outer-diameter angioscope 104 (e.g., about 1.7 French (567 micrometers) at its distal end) while providing adequate visual image resolution assistance to the user for the cerebrovascular diagnostic and treatment techniques described herein. The size and flexibility of the present angioscope 104 is important not just to allow visualization of small and tortuous intercranial vascular regions, but also to be useful within the workflows described herein, in which the angioscope 104 can be inserted into and at least partially located within a working lumen of a sheath catheter while permitting another instrument such as a coronary pathology treatment catheter 110 to also be inserted into and at least partially located within the same working lumen 108 of the sheath catheter 102. This can help enable concurrent real-time visualization and treatment, which, in turn, can help the user adjust treatment and improve efficacy. If the angioscope were too big, the physician or other user would have to insert it, view the pathology or vessel, then completely pull the too-large angioscope out, then blindly perform the treatment, and then re-insert the too-large angioscope to view the treatment location to assess efficacy. This is time-consuming and less useful in that it would not provide real-time visualization feedback concerning the treatment that might otherwise enable real-time adjustments in the treatment to improve its efficacy, as explained herein.

One approach to adapting a larger viewing instrument such as a GI endoscope to an intravascular application would be to track the viewing scope to a target intravascular location using a guidewire through a lumen of the scope. However, both an over the wire (OTW) lumen or rapid exchange (RX lumen) technique for such an approach would make the overall diameter of the device prohibitively large for cerebrovascular interventions. Moreover, an angioscope with a polyamide sheath lacks the pushability and trackability to reach a location 150 cm into the body. By contrast, the present small-diameter angioscope 104 can be housed within an outer sheath 408 that can include an embedded coil or braid, which can help improve one or more of kink resistance, pushability, and trackability. This allows the present angioscope 104 to be used within the working lumen 108 of the externally-guiding sheath catheter 102, and allows a smaller-diameter angioscope 104, such as can be capable of reaching the distant, tortuous, and small diameter cerebrovascular vessel locations, such as using one or more of the workflows described herein. The sheath catheter 102 can be advanced using a guidewire to a target location, and then the angioscope 104 can be quickly and safely advanced (without requiring a separate guidewire) via the working lumen 108 of the sheath catheter 102 up to the target cerebrovascular pathology to be diagnosed or treated. The angioscope 104 can then be further advanced, such as for a modest distance beyond the distal opening of the working lumen 108 of the sheath catheter 102, with sufficient ease to allow real-time visualization by the user even when another instrument, such as a cerebrovascular pathology treatment catheter 110 is also advanced into and co-located within the working lumen 108 of the sheath catheter 102.

In such a way, the sheath catheter 102 can be used to support the angioscope 104 in cerebrovascular interventions. The sheath catheter 102 can help guide or navigate the angioscope 104 to a target location, and its balloon 204 can be inflated to occlude blood flow and to stabilize the vessel and create a viewing window to assist with user visualization using the angioscope 104. To safely do this, the balloon design has to be more refined then it would be in peripheral vessels. The sheath catheter 102 can include a large inner diameter working lumen 108, but a small outer diameter, which together can help allow for the approach of using multiple instruments (e.g., the angioscope 104 and the cerebrovascular pathology treatment catheter 110) co-located within the working lumen 108 of the sheath catheter 102, while also permitting access to distant, small, and tortuous vessel locations such as at or near the middle cerebral artery (MCA). Quick inflation and deflation times of the balloon 204 can help the physician or other user quickly restore blood flow to the brain to avoid brain tissue damage from lack of blood perfusion. Such considerations are not as important for a non-cerebrovascular balloon catheter. In a cerebrovascular application, however, providing a large concentric inflation lumen distributed about the working lumen 108, still allows a reduced outer diameter distal to the balloon 204, which can allow distal access to a smaller vessel at locations beyond (more distal) to the balloon 204. This can help allow a distal end of the sheath catheter 102 to travel further into a reduced diameter cerebrovascular vessel than an approach this did not provide such a step-down in outer diameter for locations beyond the balloon 204, which would be difficult or impossible to advance to intracranial locations beyond the carotid artery.

Illustrative Example of A Sheath Catheter FIGS. 9A, 9B, 9C, 9D, 9E, and 9F builds upon the description of earlier-presented figures, and show various views of portions of an example of a sheath catheter 102, such as can include a distal access balloon catheter, such as can include structural features that can be particularly useful for diagnosing and treating cerebrovascular pathologies, such as at an intracerebral location beyond the petrous segment of the carotid artery. This is because such cerebrovascular pathologies present particularly difficult challenges due to blood vessel size and tortuosity, time constraints on intervention and treatment duration due to possible brain tissue ischemic or damage from lack of blood perfusion while a blood vessel is constricted or blocked such as due to a thrombosis or the use of a partially or fully-occlusive treatment device. However, the present systems, devices, and methods may also be useful for other intravascular diagnosis or treatment at locations other than cerebrovascular locations, such that the present subject matter is not limited to cerebrovascular viewing and interventional treatment.

FIG. 9A shows a top view of the sheath catheter 102, which can include an elongate body 904, such as having a distal portion 202A, a proximal portion 202B, and an intermediate portion therebetween. The proximal portion 202B can include a hub portion 902, from which the elongate body 904 can extend more distally. An inflatable balloon 204 can be located at or toward the distal portion 202A of the elongate body 904. The elongate body 904 can include a concentric arrangement that can include an outer body or outer sheath 210, such as can extend about an inner body or inner sheath 212, such as defining an annular inflation lumen 207 therebetween, such as can be seen by taking a section A-A, as shown in FIG. 9A, with an example of a sectional representation of the section A-A shown in FIG. 9C. The inner body or inner sheath 212 can define a working lumen 108 therewithin, thereby providing a concentric dual lumen structure in combination with the annular inflation lumen 207.

The inner body or inner sheath 212 can extend beyond a distal end of the balloon 204, such as by an offset distance L, such that a distal end of the balloon 204 can be offset from a distal tip of the sheath catheter 102 by an offset distance L of at least 8 millimeters, such as can help to provide additional cerebrovascular access, beyond the balloon 204, via the working lumen 108 of the inner body or inner sheath 212. In various examples, the offset distance L can be between 8 mm and 100 mm or longer, such as 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, and 100 mm. Extending the inner body or inner sheath 212, and its working lumen 108, beyond the distal end of the balloon 204 can help provide additional diagnostic or treatment access capability beyond the balloon 204, which can be particularly useful in diagnosing or treating cerebrovascular pathologies. At the distal end of the sheath catheter 102, a slight outward flared or other atraumatic tip 910 can be provided, such as shown in FIG. 9A and shown in more detail in the detail representation of FIG. 9F. The working lumen 108 can also be similarly flared, such as can be helpful for viewing or applying suction or other treatment via the working lumen.

FIG. 9B is a side view that shows an example of how the hub 902 can provide separate access to the working lumen 108 and the inflation lumen 207, such as via a working lumen access port 908 and an inflation lumen access port 907, respectively, each of which can be in fluid communication with its lumen, and each of which can include an external connector or other structure to which another instrument or other apparatus can be mechanically coupled and optionally sealed.

FIG. 9A also illustrates an example of providing a laterally stepped-down inner body or inner sheath 212 portion extending more distally beyond the balloon 204. For example, the inner body or inner sheath 212 can have a smaller outer diameter or other outer periphery than an outer diameter or other outer periphery of the outer body or outer sheath 210. The inflatable balloon 204 can be located toward a distal portion 202A of the elongate body 904 of the sheath catheter 102. The proximal end of the balloon 204 can be proximally attached to the elongate body 904 of the sheath catheter 102, such as via at least one of the outer diameter or other outer periphery of the outer body or outer sheath 210 or additionally or alternatively via a distal end face of the outer body or outer sheath 210. For example, the distal end of the outer body or outer sheath 210 can terminate at a proximal end of the balloon 204, with an optional proximal cuff that can be included to attach the proximal end of the balloon 204 to the outer body or outer sheath 210.

The balloon 204 can be distally attached to the elongate body 904 of the sheath catheter 102 such as via an outer diameter or outer periphery of the inner body or inner sheath 212, such as with an optional distal cuff that can be included to attach the distal end of the balloon 204 to the inner body or inner sheath 212.

By this manner of attaching the proximal end of the balloon 204 to the outer body or outer sheath 210 and attaching the distal end of the balloon 204 to the inner body or inner sheath 212, the elongate body 904 of the sheath catheter 102 can be dimensionally stepped-down laterally relative to the proximally attached portion of the balloon, with the stepping-down occurring in a proximal-to-distal direction, such as beyond at least the proximal end of the balloon 204, and continuing beyond the distal end of the balloon. Optionally, the atraumatic distal tip 910 can flare back out, such as to permit a lateral dimension of an outer periphery of the distal tip 910 to match a lateral dimension of the outer body or outer sheath 210, which can permit an outer periphery of the distal tip 910 to track within a lumen of another device that can also accommodate an outer periphery of the outer body or outer sheath 210. The detailed views of FIGS. 9D (side view) and 9E (side sectional view) show a distal end of the balloon 204 being attached to an outer periphery of the inner body or inner sheath 212.

The sectional views 9C and 9E help illustrate that one or both of the inner body or inner sheath 212 or the outer body or outer sheath 210 can respectively include one or more than one layers forming the inner body or inner sheath 212 or the outer body or outer sheath 210. Moreover, the particular nature of the number or materials of the layers can vary, such as along the length of the elongate body 904, such as to provide a desired bending flexibility or stiffness, or other characteristic at, that location along the length of the elongate body 904. For example, in FIG. 9C, the inner body or inner sheath 212 can include an inner layer 922, such as adjacent to and defining therewithin the working lumen 109. Adjacent to and outward from the inner layer 922, an intermediate layer 924 can be included. Adjacent to and outward from the intermediate layer 926, an outer layer can be included. Again, such layers may differ along the length of the elongate body.

FIGS. 10A (side view) and 10B (side sectional view) and 10C (detailed side sectional view at the line 10C-10C of FIG. 10B) shows an example of the inner body or inner sheath 212, together with an illustrative example of its layered construction along a length of the elongate body 904 of the sheath catheter 102, such as in illustrative Sections A, B, C, D, E, F, and G proceeding from a distal portion 202A of the inner body or inner sheath 212 of the elongate body 904 of the sheath catheter 102 toward a proximal portion 202B of the inner body or inner sheath 212 of the elongate body 904 of the sheath catheter 102. Table 1 provides additional description of FIGS. 10A, 10B, by way of example, but not by way of limitation.

TABLE 1

Illustrative embodiment of the inner body or inner sheath

| Section | Length | Inner Layer 922 | Intermediate Layer 924 | Outer Layer 926 |
|---|---|---|---|---|
| A | 1 mm-100 mm | No Liner | Metal Tube Stretched, Laser Cut | Polymer |
| B | 5 mm-300 mm | Liner Stretched | Metal Tube Stretched, Laser Cut | Polymer |
| C | 5 mm-300 mm | Liner Unstretched | Metal Tube Stretched, Laser Cut | Polymer |

TABLE 1-continued

Illustrative embodiment of the inner body or inner sheath

| Section | Length | Inner Layer 922 | Intermediate Layer 924 | Outer Layer 926 |
|---|---|---|---|---|
| D | 5 mm-300 mm | Liner Unstretched | Metal Tube Stretched, Laser Cut | Polymer |
| E | 5 mm-5000 mm | Liner Unstretched | Metal Tube UnStretched, Laser Cut | Polymer |
| F | 5 mm-1500 mm | Liner Unstretched | Metal Tube UnStretched, Laser Cut | Polymer |
| G | 5 mm-1500 mm | Liner Unstretched | Metal Braid | Polymer |

The inner layer 922 can include a PTFE or other liner, such as can help provide a desired lubricity to the inner wall of the working lumen 108. One or more portions of the liner or other inner layer 922 can be stretched, for example, by between 50% and 200%, inclusive, or another desired stretching amount, such as to provide additional bending flexibility in the stretched region. The intermediate layer 924 can include a metal hypotube, such as can include a Nitinol (e.g., nickel titanium alloy) or other structure, such as can help provide structural rigidity—including underneath the balloon 204 during inflation or elsewhere such as to help maintain patency of the inflation lumen 207 or the working lumen 108, including during inflation of the balloon 204. One or more portions of the metal tube or other intermediate layer 924 can be stretched, for example, by between 50% and 200%, inclusive, or another desired stretching amount, such as to provide additional bending flexibility in the stretched region. Additionally or alternatively, one or more portions of the metal tube or other intermediate layer 924 can be laser cut, for example, at recurring intervals, such as to provide additional bending flexibility in the stretched region. Cutting before stretching can widen the cuts, and can thereby help provide additional bending flexibility, where desired. Portions of the intermediate layer 924 can include a stainless steel or other metal or other braid, if desired. The outer layer 926 can include Pebax or Nylon or other polymer of a desired hardness (e.g., durometer between 25D and 100 D, inclusive) or stiffness, such as can vary between the different sections along the length of the inner body or inner sheath 212. One or more portions or all of the outer layer 926 can be heated and reflowed, such as after assembly with the intermediate layer 924 and the inner layer 922, such as to reflow-bond the outer layer 926 to the inner layer 922, such as through openings in the intermediate layer 924 such as provided by the cuts or braid openings.

FIGS. 11A (side view) and 11B (side sectional view) and 11C (detailed side sectional view at the line 11C-11C of FIG. 11B) shows an example of the outer body or outer sheath 210, together with an illustrative example of its layered construction along a length of the elongate body 904 of the sheath catheter 102, such as in illustrative Sections A, B, C, D, E, F, and G proceeding from a distal portion 202A of the outer body or outer sheath 210 of the elongate body 904 of the sheath catheter 102 toward a proximal portion 202B of the outer body or outer sheath 210 of the elongate body 904 of the sheath catheter 102. Table 2 provides additional description of FIGS. 11A, 11B, by way of example, but not by way of limitation.

TABLE 2

Illustrative embodiment of the outer body or outer sheath

| Section | Length | Inner Layer 932 | Intermediate Layer 934 | Outer Layer 936 |
|---|---|---|---|---|
| A-Balloon | 3 mm-35 mm | | | |
| B | 5 mm-500 mm | No Liner | Nickel Titanium Coil | Polymer |
| C | 5 mm-500 mm | Liner Unstretched | Nickel Titanium Coil | Polymer |
| D | 5 mm-500 mm | Liner Unstretched | Nickel Titanium Coil | Polymer |
| E | 5 mm-500 mm | Liner Unstretched | Nickel Titanium Coil | Polymer |
| F | 5 mm-500 mm | Liner Unstretched | Nickel Titanium Coil | Polymer |
| G | 5 mm-1500 mm | Liner Unstretched | Metal Braid | Polymer |

The inner layer 932 can include a PTFE or other liner, such as can be exposed to the inflation lumen 207. One or more portions of the liner or other inner layer 932 can be stretched, for example, by between 50% and 200%, inclusive, or another desired stretching amount, such as to provide additional bending flexibility in the stretched region, if desired. The intermediate layer 934 can include a metal (e.g., nickel titanium alloy) coil or braid (e.g., stainless steel) or other structure, such as can help provide structural rigidity. One or more portions of the intermediate layer 934 can be stretched, for example, by between 50% and 200%, inclusive, or another desired stretching amount, such as to provide additional bending flexibility in the stretched region, if desired. Portions of the intermediate layer 934 can include a stainless steel or other metal or other braid, if desired. The outer layer 936 can include Pebax or Nylon or other polymer of a desired hardness (e.g., durometer between 25D and 100 D, inclusive) or stiffness, such as can vary between the different sections along the length of the outer body or outer sheath 210. One or more portions or all of the outer layer 936 can be heated and reflowed, such as after assembly with the intermediate layer 934 and the inner layer 932, such as to reflow-bond the outer layer 936 to the inner layer 932, such as through openings in the intermediate layer 934 such as provided by the coil interstices or braid openings.

The stretching described herein can thin the resulting material. The stretching or thinning, by itself, or in combination with the cutting or scoring (e.g., transverse to the longitudinal direction of the elongate body 904 can help provide additional bending flexibility in one or more desired regions of the elongate body. For example, the stretching of the PTFE liner 922, 932 can result in a thickness of the PTFE liner 922, 932 of (0.5/1000) inch, which can be much thinner than other available materials, such as an unstretched liner material having a thickness of (0.75/1000) inch.

The above description has emphasized systems, devices, and methods for diagnosing and treating cerebrovascular pathologies, such as at an intracerebral location beyond the petrous segment of the carotid artery. This is because such cerebrovascular pathologies present particularly difficult challenges due to blood vessel size and tortuosity, time constraints on intervention and treatment duration due to possible brain tissue ischemia or damage from lack of blood perfusion while a blood vessel is constricted or blocked such as due to a thrombosis or the use of a partially or fully-occlusive treatment device. However, the present systems, devices, and methods may also be useful for other intravascular diagnosis or treatment at locations other than cerebrovascular locations, such that the present subject matter is not limited to cerebrovascular viewing and interventional treatment.

The above description includes references to the accompanying drawings, which form a part of the detailed description. The drawings show, by way of illustration, specific embodiments in which the invention can be practiced. These embodiments are also referred to herein as "examples" or "aspects", an illustrative non-limiting numbered list of which is provided below.

Aspect 1 can include or use subject matter (such as an apparatus, a system, a device, a method, a means for performing acts, or a device readable medium including instructions that, when performed by the device, can cause the device to perform acts, or an article of manufacture), such as can include or use an apparatus to assist a user in internally both viewing and treating a cerebrovascular pathology. The apparatus can include a sheath catheter. The sheath catheter can include an elongate body defining an internal working lumen extending between a proximal portion and a distal portion of the elongate body of the sheath catheter. The sheath catheter can include an inflatable balloon, such as can be located toward a distal portion of the elongate body of the sheath catheter. The sheath catheter can include an inflation lumen, such as extending between a proximal portion of the elongate body of the sheath catheter and the balloon such as to provide fluid communication to the balloon to permit inflation and deflation of the balloon. For example, a distal portion of the elongate body of the sheath catheter can have an outer diameter between 3.5 French and 8.0 French. For example, the elongate body of the sheath catheter can define the working lumen having an inner diameter being in a range between 0.039 inches (0.99 millimeters) and 0.082 inches (2.08 millimeters), inclusive, such as a nominal or preferred value of at least 0.070 inches, such as to allow cerebrovascular treatment via the working lumen while at least a portion of an angioscope is located within the working lumen.

Aspect 2 can include or use, or can optionally be combined with the subject matter of Aspect 1 to include or use, a forward-viewing fiberoptic angioscope. The angioscope can be sized and shaped to be inserted from a proximal portion of the sheath catheter into the working lumen of the sheath catheter, such as to allow a distal portion of the angioscope to extend beyond a distal opening of the working lumen of the sheath catheter, such as to permit a user to forwardly view and inspect the cerebrovascular pathology using the angioscope.

Aspect 3 can include or use, or can optionally be combined with the subject matter of one or more of Aspects 1 or 2 to include or use an angioscope that can include a coherent fiber bundle of imaging optical fibers, such as extending between proximal and distal portion of the angioscope. For example, individual ones of the imaging fibers can have an outer diameter of about 2.5 micrometers. An uncladded arrangement of illumination fibers can be concentrically arranged around the imaging fibers. Individual ones of the illumination fibers can have an outer diameter between 25 micrometers and 50 micrometers. In an example, an outer diameter of the angioscope 104 can be less than or equal to 1.7 French at its distal end. In an example, an outer diameter of the angioscope 104 can be less than or equal to 2.4 French at its proximal end.

Aspect 4 can include or use, or can optionally be combined with the subject matter of one or more of Aspects 1 through 3 to include or use an angioscope that can include a GRIN lens or other lens, such as can be located at a distal end of the angioscope. In an example, the lens can have a diameter of 250 micrometers or less.

Aspect 5 can include or use, or can optionally be combined with the subject matter of one or more of Aspects 1 through 4 to include or use a polymer sheath that can be located at a distal portion of the angioscope, such as to concentrically surround the illumination fibers, the imaging fibers, and the GRIN lens.

Aspect 6 can include or use, or can optionally be combined with the subject matter of one or more of Aspects 1 through 5 to include or use a clot-resistant coating material, such as can be located on the GRIN lens or other lens.

Aspect 7 can include or use, or can optionally be combined with the subject matter of one or more of Aspects 1 through 6 to include or use a common cladding such as can be located or shared between individual ones of the imaging fibers.

Aspect 8 can include or use, or can optionally be combined with the subject matter of one or more of Aspects 1 through 7 to include or use a polymeric jacket that can provide one or more of a coating or an encapsulation of the imaging fibers.

Aspect 9 can include or use, or can optionally be combined with the subject matter of one or more of Aspects 1 through 8 to include or use a proximal portion of the sheath catheter that can be stiffer than a more distal portion of the sheath catheter.

Aspect 10 can include or use, or can optionally be combined with the subject matter of one or more of Aspects 1 through 9 to include or use the sheath catheter including at least two different portions (e.g., lengths) having different durometers or stiffnesses.

Aspect 11 can include or use, or can optionally be combined with the subject matter of one or more of Aspects 1 through 10 to include or use the elongate body of the sheath catheter including at least one of a braid or a coil. The braid or coil can be configured to be less stiff toward a distal portion of the elongate body than toward a more proximal portion of the elongate body.

Aspect 12 can include or use, or can optionally be combined with the subject matter of one or more of Aspects 1 through 11 to include or use the at least one of the braid or the coil including a metal or nylon material (e.g., such as can be stiffer than and provide reinforcement to a softer adjacent covering or encapsulating material).

Aspect 13 can include or use, or can optionally be combined with the subject matter of one or more of Aspects 1 through 12 to include or use the at least one of the braid or the coil terminating short of a distal end of the elongate body of the sheath catheter to allow relatively greater flexibility of a distal portion of the elongate body.

Aspect 14 can include or use, or can optionally be combined with the subject matter of one or more of Aspects 1 through 13 to include or use the working lumen of the sheath catheter being coated or filled with or otherwise carries a hydrophilic lubricious material (e.g., such as by providing a Teflon® or other polytetrafluoroethylene or other liner).

Aspect 15 can include or use, or can optionally be combined with the subject matter of one or more of Aspects 1 through 14 to include or use a valve, such as can be located toward a proximal portion of the sheath catheter. The valve can be configured to allow a. vacuum to be built up behind the valve and then applied to the working lumen of the sheath catheter upon opening the valve, such as to permit applying sudden suction at a distal end of the working lumen of the sheath catheter.

Aspect 16 can include or use, or can optionally be combined with the subject matter of one or more of Aspects 1 through 15 to include or use a cerebrovascular pathology treatment catheter, such as can be sized and shaped to extend through the working lumen of the sheath catheter, such as while allowing at least a portion of the angioscope to also remain within the working lumen of the sheath catheter.

Aspect 17 can include or use, or can optionally be combined with the subject matter of one or more of Aspects 1 through 16 to include or use the cerebrovascular pathology treatment catheter including a thrombus retriever catheter (e.g., such as a stent retriever or the like).

Aspect 18 can include or use, or can optionally be combined with the subject matter of one or more of Aspects 1 through 17 to include or use the thrombus retriever catheter including a stent or other engagement mechanism at a distal end of the thrombus retriever catheter. In an example, the stent or other engagement mechanism can be configured to expand into or otherwise engage with a thrombus such as can be located in vasculature beyond a distal opening of the working lumen of the sheath catheter.

Aspect 19 can include or use, or can optionally be combined with the subject matter of one or more of Aspects 1 through 18 to include or use the thrombus retriever catheter including a longitudinal guidewire lumen, such as can be sized and shaped to accommodate a guidewire therein, such as to allow the thrombus retriever catheter to be extended over the guidewire, e.g., such as through the working lumen of the sheath catheter.

Aspect 20 can include or use, or can optionally be combined with the subject matter of one or more of Aspects 1 through 19 to include or use the cerebrovascular pathology treatment catheter including an aspiration catheter, such as including an elongate body defining a longitudinal aspiration lumen.

Aspect 21 can include or use, or can optionally be combined with the subject matter of one or more of Aspects 1 through 20 to include or use a method for internally both viewing and treating a cerebrovascular pathology. The method can include advancing a sheath catheter through vasculature toward the pathology to be treated. A distal balloon of the sheath catheter can then be inflated, such as to occlude a region of the vasculature to stabilize a distal portion of the sheath catheter. A distal tip of a forward-viewing fiberoptic angioscope can be extended, such as via a working lumen of the sheath catheter, such as to forwardly view and inspect the pathology using the angioscope. The cerebrovascular pathology can then be treated, such as via a working lumen of the sheath catheter, while allowing at least a portion of the angioscope to remain within the working lumen of the sheath catheter. Then, further viewing can optionally be carried out, such as via the distal tip of the angioscope, such as for viewing a location beyond a distal opening of the working lumen of the sheath catheter. Such forward toward the vasculature can help the user to assess the cerebrovascular pathology treatment.

Aspect 22 can include or use, or can optionally be combined with the subject matter of one or more of Aspects 1 through 21 to include or use treating the cerebrovascular pathology including inserting a cerebrovascular treatment catheter via the working lumen of the sheath catheter while allowing at least a portion of the angioscope to remain within the working lumen of the sheath catheter.

Aspect 23 can include or use, or can optionally be combined with the subject matter of one or more of Aspects 1 through 22 to include or use advancing the sheath catheter, wherein the sheath catheter can have an outer diameter between 3.5 French and 8.0 French. An inner diameter of the working lumen of the sheath catheter can be in a range between 0.039 inches (0.99 millimeters) and 0.082 inches (2.08 millimeters), inclusive, such as a nominal or preferred value of at least 0.070 inches. This can allow at least a portion of a cerebrovascular pathology treatment catheter and at least a portion of the angioscope to both remain within the working lumen of the sheath catheter.

Aspect 24 can include or use, or can optionally be combined with the subject matter of one or more of Aspects 1 through 23 to include or use inflating a distal balloon of the sheath catheter, such as can include occluding blood flow using the inflated distal balloon.

Aspect 25 can include or use, or can optionally be combined with the subject matter of one or more of Aspects 1 through 24 to include or use injecting a saline or other fluid via the working lumen of the sheath catheter such as after inflating the distal balloon of the sheath catheter, the fluid being transparent such as to permit viewing using the angioscope.

Aspect 26 can include or use, or can optionally be combined with the subject matter of one or more of Aspects 1 through 25 to include or use the cerebrovascular pathology including a thrombus, and wherein inserting a cerebrovascular pathology treatment catheter includes extending a thrombus retrieval catheter beyond the distal opening of the working lumen of the sheath catheter. This can permit collecting and removing at least a portion of the thrombus by retracting the thrombus retrieval catheter through the working lumen of the sheath catheter, such as while allowing at least a portion of the angioscope to remain within the working lumen of the sheath catheter.

Aspect 27 can include or use, or can optionally be combined with the subject matter of one or more of Aspects 1 through 26 to include or use inserting a guidewire via the working lumen of the sheath catheter before inserting the thrombus retrieval catheter. The thrombus retrieval catheter can be inserted over the guidewire, such as while at least a portion of the angioscope remains within the working lumen of the sheath catheter.

Aspect 28 can include or use, or can optionally be combined with the subject matter of one or more of Aspects 1 through 27 to include or use inserting the guidewire including crossing the thrombus via a distal tip of the guidewire, such as before inserting the thrombus retrieval catheter such as over the guidewire.

Aspect 29 can include or use, or can optionally be combined with the subject matter of one or more of Aspects 1 through 28 to include or use inserting the thrombus retrieval catheter over the guidewire including inserting a distal end of the thrombus retrieval catheter, such as over the guidewire and into or beyond the thrombus.

Aspect 30 can include or use, or can optionally be combined with the subject matter of one or more of Aspects 1 through 29 to include or use retracting the guidewire through the working lumen of the sheath catheter such as while at least a portion of the thrombus retrieval catheter and at least a portion of the angioscope remain within the working lumen of the sheath catheter.

Aspect 31 can include or use, or can optionally be combined with the subject matter of one or more of Aspects 1 through 30 to include or use retracting the thrombus retrieval catheter through the working lumen of the sheath catheter such as while at least a portion of the angioscope remains within the working lumen of the sheath catheter.

Aspect 32 can include or use, or can optionally be combined with the subject matter of one or more of Aspects 1 through 31 to include or use again inserting a cerebrovascular pathology treatment catheter via a working lumen of the sheath catheter when the assessment of the cerebrovascular pathology treatment using the angioscope indicates a need for further treatment.

Aspect 33 can include or use, or can optionally be combined with the subject matter of one or more of Aspects 1 through 32 to include or use again inserting the cerebrovascular pathology treatment catheter via a working lumen of the sheath catheter including inserting another cerebrovascular pathology treatment catheter.

Aspect 34 can include or use, or can optionally be combined with the subject matter of one or more of Aspects 1 through 33 to include or use again inserting the cerebrovascular pathology treatment catheter via a working lumen of the sheath catheter includes inserting a different type of cerebrovascular pathology treatment catheter.

Aspect 35 can include or use, or can optionally be combined with the subject matter of one or more of Aspects 1 through 34 to include or use aspirating via a working lumen of the sheath catheter when the assessment of the cerebrovascular pathology treatment using the angioscope indicates a need for further treatment.

Aspect 36 can include or use, or can optionally be combined with the subject matter of one or more of Aspects 1 through 35 to include or use the aspirating being carried out before deflating the distal balloon of the sheath catheter.

Aspect 37 can include or use, or can optionally be combined with the subject matter of one or more of Aspects 1 through 36 to include or use inserting a guidewire via the working lumen of the sheath catheter before inserting the cerebrovascular treatment catheter. The cerebrovascular treatment catheter can be inserted over the guidewire, while at least a portion of the angioscope remains within the working lumen of the sheath catheter.

Aspect 38 can include or use, or can optionally be combined with the subject matter of one or more of Aspects 1 through 37 to include or use the cerebrovascular pathology including an aneurysm. Inserting the cerebrovascular pathology treatment catheter can include inserting an aneurysm thrombolytic occluder via the working lumen of the sheath catheter into the aneurysm while allowing at least a portion of the angioscope to remain within the working lumen of the sheath catheter.

Aspect 39 can include or use, or can optionally be combined with the subject matter of one or more of Aspects 1 through 38 to include or use the aneurysm thrombolytic occluder being used to dispose one or more aneurysm coils into the aneurysm while intravascularly viewing, using the angioscope, the disposing of the one or more aneurysm coils into the aneurysm.

Aspect 40 can include or use, or can optionally be combined with the subject matter of one or more of Aspects 1 through 39 to include or use inserting a guidewire via the working lumen of the sheath catheter before inserting the aneurysm thrombolytic occlude. The aneurysm thrombolytic occluder can then be inserted over the guidewire, such as while at least a portion of the angioscope remains within the working lumen of the sheath catheter.

Aspect 41 can include or use, or can optionally be combined with the subject matter of one or more of Aspects 1 through 40 to include or use inserting the guidewire including inserting a distal tip of the guidewire into the aneurysm before inserting the aneurysm thrombolytic occluder over the guidewire.

Aspect 42 can include or use, or can optionally be combined with the subject matter of one or more of Aspects 1 through 41 to include or use retracting the guidewire through the working lumen of the sheath catheter, such as while at least a portion of the aneurysm thrombolytic occluder and at least a portion of the angioscope remain within the working lumen of the sheath catheter.

Aspect 43 can include or use, or can optionally be combined with the subject matter of one or more of Aspects 1 through 42 to include or use retracting the aneurysm thrombolytic occluder through the working lumen of the sheath catheter, such as while at least a portion of the angioscope remains within the working lumen of the sheath catheter.

Aspect 44 can include or use, or can optionally be combined with the subject matter of one or more of Aspects 1 through 43 to include or use the aneurysm thrombolytic occluder introducing a liquid embolic or other thrombolytic agent into the aneurysm, such as while intravascularly viewing, using the angioscope, the disposing of the thrombolytic agent into the aneurysm.

Aspect 45 can include or use, or can optionally be combined with the subject matter of one or more of Aspects 1 through 44 to include or use the aneurysm thrombolytic occluder including a fluid delivery catheter, and further comprising introducing the thrombolytic agent into the aneurysm via a working lumen of the fluid delivery catheter with a distal tip of the fluid delivery catheter located within the aneurysm.

Aspect 46 can include or use, or can optionally be combined with the subject matter of one or more of Aspects 1 through 45 to include or use the fluid delivery catheter being introduced over a guidewire to locate a distal tip of the fluid delivery catheter within the aneurysm.

Aspect 47 can include or use, or can optionally be combined with the subject matter of one or more of Aspects 1 through 46 to include or use the fluid delivery catheter for introducing a thrombolytic agent into the aneurysm after introducing one or more aneurysm coils into the aneurysm.

Aspect 48 can include or use, or can optionally be combined with the subject matter of one or more of Aspects 1 through 47 to include or use the cerebrovascular pathology including a thrombus. in an example, inserting a cerebrovascular pathology treatment catheter can include extending a thrombus aspiration catheter, such as beyond the distal opening of the working lumen of the sheath catheter, such as for collecting and removing at least a portion of the thrombus such as by aspirating the thrombus such as via the thrombus aspiration catheter located within the working lumen of the sheath catheter, such as while allowing at least a portion of the angioscope to remain within the working lumen of the sheath catheter.

Aspect 49 can include or use, or can optionally be combined with the subject matter of one or more of Aspects 1 through 48 to include or use aspirating the thrombus including corking the thrombus such as via a distal tip of thrombus aspiration catheter such as before retracting the thrombus aspiration catheter through the working lumen of the sheath catheter such as while at least a portion of the angioscope remains within the working lumen of the sheath catheter.

Aspect 50 can include or use, or can optionally be combined with the subject matter of one or more of Aspects 1 through 49 to include or use inserting a guidewire via the working lumen of the sheath catheter such as before inserting the thrombus aspiration catheter. The thrombus aspiration catheter can be inserted over the guidewire, such as while at least a portion of the angioscope remains within the working lumen of the sheath catheter.

Aspect 51 can include or use, or can optionally be combined with the subject matter of one or more of Aspects 1 through 50 to include or use retracting the guidewire through the working lumen of the sheath catheter such as while at least a portion of the thrombus aspiration catheter and at least a portion of the angioscope remain within the working lumen of the sheath catheter.

Aspect 52 can include or use, or can optionally be combined with the subject matter of one or more of Aspects 1 through 51 to include or use aspirating at least a portion of the thrombus into the thrombus aspiration catheter and retracting the thrombus aspiration catheter through the working lumen of the sheath catheter such as while at least a portion of the angioscope remains within the working lumen of the sheath catheter.

Aspect 53 can include or use, or can optionally be combined with the subject matter of one or more of Aspects 1 through 52 to include or use, after retracting the thrombus aspiration catheter, aspirating again via a working lumen of the sheath catheter while viewing using the angioscope.

Aspect 54 can include or use, or can optionally be combined with the subject matter of one or more of Aspects 1 through 53 to include or use the aspirating being carried out before deflating the distal balloon of the sheath catheter. Then the distal balloon of the sheath catheter can be deflated.

Aspect 55 can include or use, or can optionally be combined with the subject matter of one or more of Aspects 1 through 54 to include or use a method for internally both viewing and treating a cerebrovascular thrombus. The method can include advancing a sheath catheter through vasculature toward the thrombus to be treated. A distal balloon of the sheath catheter can then be deflated, such as to occlude a region of the vasculature, such as to stabilize a distal portion of the sheath catheter. A distal tip of a forward-viewing fiberoptic angioscope can then be extended to or even beyond a distal opening of a working lumen of the sheath catheter to forwardly view and inspect the thrombus using the angioscope. A thrombus retrieval catheter can then be extended beyond the distal opening of the working lumen of the sheath catheter, such as for collecting and removing at least a portion of the thrombus, such as by retracting the thrombus retrieval catheter through the working lumen of the sheath catheter while allowing at least a portion of the angioscope to remain within the working lumen of the sheath catheter. The extended distal tip of the angioscope can then be used, such as from a location toward, near, or even beyond the distal opening of the working lumen of the sheath catheter, such as for viewing forward toward the vasculature to assess the collecting and removing of at least a portion of the thrombus.

Aspect 56 can include or use, or can optionally be combined with the subject matter of one or more of Aspects 1 through 55 to include or use a method for internally both viewing and treating a cerebrovascular thrombus. The method can include advancing a sheath catheter through vasculature toward the thrombus to he treated. A distal balloon of the sheath catheter can then be inflated, such as to occlude a region of the vasculature, such as to stabilize a distal portion of the sheath catheter. A distal tip of a forward-viewing fiberoptic angioscope can be extended, such as via a working lumen of the sheath catheter, such as to forwardly view and inspect the thrombus using the angioscope; A vacuum can be applied, such as via a distal opening of the working lumen of the sheath catheter, such as for collecting and removing at least a portion of the thrombus, such as while allowing at least a portion of the angioscope to remain within the working lumen of the sheath catheter during the collecting and removing. The distal tip of the angioscope can be positioned at a location at, near, or even beyond the distal opening of the working lumen of the sheath catheter such as for viewing forward toward the vasculature to assess the collecting and removing of at least a portion of the thrombus.

Aspect 57 can include or use, or can optionally be combined with the subject matter of one or more of Aspects 1 through 56 to include or use advancing the sheath catheter. In an example, the sheath catheter can have an outer diameter between 3.5 French and 8.0 French, In an example, the sheath catheter can define an inner diameter of the working lumen of the sheath catheter being in a range between 0.039 inches (0.99 millimeters) and 0.082 inches (2.08 millimeters), inclusive, such as a nominal or preferred value of at least 0.070 inches, such as to allow aspiration of the thrombus via the working lumen of the sheath catheter such as while at least a portion of the angioscope remains within the working lumen of the sheath catheter.

Aspect 58 can include or use, or can optionally be combined with the subject matter of one or more of Aspects 1 through 57 to include or use inflating a distal balloon of the sheath catheter including occluding blood flow using the inflated distal balloon.

Aspect 59 can include or use, or can optionally be combined with the subject matter of one or more of Aspects 1 through 58 to include or use injecting a saline or other fluid such as via the working lumen of the sheath catheter after inflating distal balloon of the sheath catheter. The fluid can be transparent to permit viewing using the angioscope.

Aspect 60 can include or use, or can optionally be combined with the subject matter of one or more of Aspects 1 through 59 to include or use retracting a distal tip of the angioscope into the working lumen of the sheath catheter, such as before applying the vacuum via the distal opening of the working lumen of the sheath catheter.

Aspect 61 can include or use, or can optionally be combined with the subject matter of one or more of Aspects 1 through 60 to include or use observing, using the angioscope, that the thrombus has not been fully drawn into the working lumen of the sheath catheter. In response, the balloon can be deflated and the sheath catheter can be gently withdrawn with vacuum still applied to a. working lumen of the sheath catheter such as to maintain the thrombus against the distal end of the sheath for withdrawal of the thrombus under vacuum together with withdrawal of the sheath catheter.

Aspect 62 can include or use, or can optionally be combined with the subject matter of one or more of Aspects 1 through 61 to include or use applying the vacuum including building up a suction before opening a valve to apply the vacuum.

Aspect 63 can include or use, or can optionally be combined with the subject matter of one or more of Aspects 1 through 62 to include or use a method for internally both viewing and treating a cerebrovascular aneurysm. The method can include advancing a sheath catheter through vasculature toward the aneurysm to be treated. A distal balloon of the sheath catheter can be inflated, such as to occlude a region of the vasculature such as to stabilize a distal portion of the sheath catheter. A distal tip of a forward-viewing fiberoptic angioscope can be extended, such as via a working lumen of the sheath catheter such as to forwardly view and inspect the aneurysm using the angioscope. An aneurysm thrombolytic occluder can be inserted, such as via the working lumen of the sheath catheter, such as into the aneurysm such as while allowing at least a portion of the angioscope to remain within the working lumen of the sheath catheter. A distal tip of the angioscope can be extended to a location at, near, or beyond a distal opening of the working lumen of the sheath catheter, such as for viewing forward toward the vasculature such as to assess the occluder insertion into the aneurysm.

Aspect 64 can include or use, or can optionally be combined with the subject matter of one or more of Aspects 1 through 63 to include or use a cerebrovascular apparatus such as for at least partial insertion into the cerebrovasculature. The apparatus can comprise a sheath catheter. The sheath catheter can include an elongate body. The elongate body can comprise an elongate outer body and an elongate inner body having a smaller outer periphery than an outer periphery of the outer body. An inflation lumen can be defined between the outer body and the inner body. An internal working lumen can he defined within the inner body. The working lumen can extend between the proximal portion and the distal portion of the elongate body of the sheath catheter. An inflatable balloon can be located toward a distal portion of the elongate body of the sheath catheter. The balloon can be proximally attached to the elongate body of the sheath catheter such as via at least one of the outer periphery or a distal face of the outer body. The balloon can be distally attached to the elongate body of the sheath catheter such as via at least the outer periphery of the inner body such as to be dimensionally stepped-down laterally relative to the proximally attached portion of the inflation balloon. The inflation lumen can extend between the proximal portion of the elongate body of the sheath catheter and the balloon such as to provide fluid communication to the balloon to permit inflation of the balloon.

Aspect 65 can include or use, or can optionally be combined with the subject matter of one or more of Aspects 1 through 64 to include or use a distal end of the balloon that can be offset from a distal tip of the sheath catheter such as by an offset distance of at least 8 millimeters such as to provide additional cerebrovascular access, beyond the balloon, such as via the working lumen of the inner body.

Aspect 66 can include or use, or can optionally be combined with the subject matter of one or more of Aspects 1 through 65 to include or use an inner lateral dimension of the working lumen at or near the distal tip of the sheath catheter that can be larger than in a more proximal region of the working lumen.

Aspect 67 can include or use, or can optionally be combined with the subject matter of one or more of Aspects 1 through 66 to include or use a lateral outer dimension of an outer periphery of the distal tip of the sheath catheter being equal to a lateral outer dimension of the outer periphery of the outer body of the sheath catheter.

Aspect 68 can include or use, or can optionally be combined with the subject matter of one or more of Aspects 1 through 67 to include or use a sheath catheter in which the inner body can include a metal tube, such as can include extending under the balloon, such as to inhibit collapse and maintain patency of the working channel such as when an inflation pressure is applied to inflate the balloon.

Aspect 69 can include or use, or can optionally be combined with the subject matter of one or more of Aspects 1 through 68 to include or use the metal tube including a nickel titanium alloy.

Aspect 70 can include or use, or can optionally be combined with the subject matter of one or more of Aspects 1 through 69 to include or use the metal tube such as can include laser cuts such as to increase its bending flexibility.

Aspect 71 can include or use, or can optionally be combined with the subject matter of one or more of Aspects 1 through 70 to include or use more closely spaced laser cuts in a relatively more distal portion of the tube than in a relatively more proximal portion of the tube such as to provide relatively more bending flexibility in the relatively more distal portion of the tube than in the relatively more proximal portion of the tube.

Aspect 72 can include or use, or can optionally be combined with the subject matter of one or more of Aspects 1 through 71 to include or use a relatively more distal portion of the metal tube that can be stretched thinner than a relatively more proximal portion of the tube such as to yield wider laser cuts in the relatively more distal portion of the tube than in the relatively more proximal portion of the tube.

Aspect 73 can include or use, or can optionally be combined with the subject matter of one or more of Aspects 1 through 72 to include or use a relatively more distal portion of the tube that can be stretched with respect to a relatively more proximal portion of the tube such as to provide relatively more bending flexibility in the relatively more distal portion of the tube than in the relatively more proximal portion of the tube.

Aspect 74 can include or use, or can optionally be combined with the subject matter of one or more of Aspects 1 through 73 to include or use a sheath catheter that can include the inner body that can further comprise a liner within the metal tube such as along at least a portion of the tube such as to provide a desired lubricity to the inner working lumen of the sheath catheter.

Aspect 75 can include or use, or can optionally be combined with the subject matter of one or more of Aspects 1 through 74 to include or use the liner being absent in at least a portion of a distal end region of the tube that is more distal than the balloon.

Aspect 76 can include or use, or can optionally be combined with the subject matter of one or more of Aspects 1 through 75 to include or use a relatively more distal portion of the liner that can be stretched with respect, to a relatively more proximal portion of the liner such as to provide relatively more bending flexibility in the relatively more distal portion of the liner than in the relatively more proximal portion of the liner.

Aspect 77 can include or use, or can optionally be combined with the subject matter of one or more of Aspects 1 through 76 to include or use a sheath catheter in which the inner body can include at least one of a metal braid or a metal coil such as in a more proximal region of the inner body than the tube.

Aspect 78 can include or use, or can optionally be combined with the subject matter of one or more of Aspects 1 through 77 to include or use a sheath catheter in which the inner body can include a polymer outer covering adjacent to the tube and adjacent to the at least one of a metal braid or a metal coil.

Aspect 79 can include or use, or can optionally be combined with the subject matter of one or more of Aspects 1 through 78 to include or use a sheath catheter in which the inner body can further comprise a liner within the tube along at least a portion of the tube such as to provide a desired lubricity to the inner working lumen of the sheath catheter. The polymer outer covering can be reflowed to bond with the liner such as through engagement of the liner such as via a surface morphology of at least one of the tube or the braid or other intermediate layer between the liner and the outer covering.

Aspect 80 can include or use, or can optionally be combined with the subject matter of one or more of Aspects 1 through 79 to include or use a sheath catheter that can include an inner body in which a relatively more proximal portion of the polymer outer covering can include a stiffer material than a relatively more distal portion of the polymer outer covering.

Aspect 81 can include or use, or can optionally be combined with the subject matter of one or more of Aspects 1 through 80 to include or use a sheath catheter that can include an inner body in which a relatively more proximal portion of the polymer outer covering can include a harder material than a relatively more distal portion of the polymer outer covering.

Aspect 82 can include or use, or can optionally be combined with the subject matter of one or more of Aspects 1 through 81 to include or use a sheath catheter, such as wherein at least a portion of its outer body can include: an inner liner; an intermediate later that can include one of a metal coil or metal braid extending along and around the inner liner; and an outer layer such as a polymer outer covering extending along and around the one of the coil or braid of the outer body.

Aspect 83 can include or use, or can optionally be combined with the subject matter of one or more of Aspects 1 through 82 to include or use a sheath catheter that can include an outer body that can include the polymer outer covering being reflowed to bond with the inner liner of the outer body such as through engagement of the inner liner of the outer body via a surface morphology of at least one of the coil or the braid of the outer body.

Aspect 84 can include or use, or can optionally be combined with the subject matter of one or more of Aspects 1 through 83 to include or use the coil of the outer body such as can include a nickel titanium alloy.

Aspect 85 can include or use, or can optionally be combined with the subject matter of one or more of Aspects 1 through 84 to include or use a cerebrovascular apparatus such as for at least partial insertion into the cerebrovasculature. The apparatus can comprise a sheath catheter. The sheath catheter can include an elongate body. The elongate body can comprise an elongate outer body and an elongate inner body having a smaller outer periphery than an outer periphery of the outer body. An inflation lumen can be defined between the outer body and the inner body. An internal working lumen can be defined within the inner body. An inflatable balloon can be located toward a distal portion of the elongate body of the sheath catheter. The inflation lumen can extend between the proximal portion of the elongate body of the sheath catheter and the balloon such as to provide fluid communication to the balloon to permit inflation of the balloon. The working lumen can extend between the proximal portion and the distal portion of the elongate body of the sheath catheter and the working lumen further extends to a distal tip of the sheath catheter that is offset from a distal end of the balloon by an offset distance of at least 8 millimeters to provide additional cerebrovascular access beyond the balloon via the working lumen of the inner body.

Aspect 85 can include or use, or can optionally be combined with the subject matter of one or more of Aspects 1 through 84 to include or use a cerebrovascular apparatus such as for at least partial insertion into the cerebrovasculature. The apparatus can comprise a sheath catheter. The sheath catheter can include an elongate body. The elongate body can comprise an elongate outer body and an elongate inner body having a smaller outer periphery than an outer periphery of the outer body. An internal working lumen can be defined within the inner body, such as can extend between the proximal portion and the distal portion of the elongate body of the sheath catheter. At least one of the inner body or the outer body can include at least a portion that is stretched relative to an other portion of said at least one of the inner body or the outer body such as to provide greater relative bending flexibility in the stretched portion relative to the other portion.

Aspect 85 can include or use, or can optionally be combined with the subject matter of one or more of Aspects 1 through 84 to include or use a cerebrovascular apparatus such as for at least partial insertion into the cerebrovasculature. The apparatus can comprise a sheath catheter. The sheath catheter can include an elongate body. The elongate body can comprise an elongate outer body and an elongate inner body having a smaller outer periphery than an outer periphery of the outer body. An internal working lumen can be defined within the inner body, The working lumen can extend between the proximal portion and the distal portion of the elongate body of the sheath catheter. At least one of the inner body or the outer body can include at least a region having an inner portion and an outer portion that can be bonded together such as via a reflow bond such as extending through a surface morphology of an intermediate portion located between the inner portion and the outer portion.

Aspect 86 can include or use, or can optionally be combined with the subject matter of one or more of Aspects 1 through 85 to include or use a cerebrovascular apparatus such as for at least partial insertion into the cerebrovasculature. The apparatus can comprise a sheath catheter. The sheath catheter can include an elongate body. The elongate body can comprise an elongate outer body and an elongate inner body having a smaller outer periphery than an outer periphery of the outer body. An inflation lumen can be defined between the outer body and the inner body. An internal working lumen can be defined within the inner body. The internal working lumen can extend between the proximal portion and the distal portion of the elongate body of the sheath cathete. An inflatable balloon can be located toward a distal portion of the elongate body of the sheath catheter. An inflation lumen can extend between the proximal portion of the elongate body of the sheath catheter and the balloon such as to provide fluid communication to the balloon such as to permit inflation or deflation of the balloon. The inner body can include a metal tube, including extending under the balloon, such as to inhibit collapse and maintain patency of the working channel when an inflation pressure is applied to inflate the balloon.

Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A cerebrovascular apparatus for at least partial insertion into a cerebrovasculature, the apparatus comprising:
   a sheath catheter, including:
   an elongate body, comprising an elongate outer body and an elongate inner body having a smaller outer periphery than an outer periphery of the outer body, an inflation lumen defined between the outer body and the inner body, an internal working lumen defined within the inner body, the working lumen extending between an opening at a proximal portion and an opening at a distal portion of the elongate body of the sheath catheter;
   an inflatable inflation balloon, located toward a distal portion of the elongate body of the sheath catheter, the balloon proximally attached to the elongate body of the sheath catheter via at least one of the outer periphery or a distal face of the outer body, the balloon distally attached to the elongate body of the sheath catheter via at least the outer periphery of the inner body so as to be dimensionally stepped-down laterally relative to a more proximally attached portion of a distal cuff of the inflation balloon, wherein the balloon is made of a compliant material configured to be expanded at a desired cerebrovascular location at which to stabilize the apparatus;
   wherein the inflation lumen extends between the proximal portion of the elongate body of the sheath catheter and the balloon to provide fluid communication to the balloon to permit inflation of the balloon; and
   wherein a distal end of a distal cuff of the balloon is offset, by the internal working lumen being a single sidewall-hole free closed-tubular-walled fluid-communicating suction lumen tube, from a distal tip of the sheath catheter by an offset distance of at least 8 millimeters and an outer diameter of less than 8 French to provide additional cerebrovascular access and suction, beyond the balloon, via the closed-tubular-walled suction lumen tube into the working lumen of the inner body to permit suctioning of a cerebrovascular clot via the closed-tubular-walled suction lumen, and
   wherein an inner lateral dimension of the working lumen at or near the distal tip of the sheath catheter flares outward in a distal direction to become larger in orifice than in a more proximal region of the working lumen.

2. The apparatus of claim 1, wherein a lateral outer dimension of an outer periphery of the distal tip of the sheath catheter flares outward in a distal direction to become equal to a lateral outer dimension of the outer periphery of the outer body of the sheath catheter.

3. The apparatus of claim 1, wherein the inner body includes a stretched cylindrical metal tube, including stretching extending under the balloon, the stretching by between 50% and 200% inclusive, inhibit collapse and maintain patency of the working lumen when an inflation pressure is applied to inflate the balloon.

4. The apparatus of claim 3, wherein the tube includes variable spacing laser cuts in the stretched cylindrical metal tube to increase its bending flexibility.

5. The apparatus of claim 4, including more closely spaced laser cuts in a relatively more distal portion of the stretched cylindrical metal tube than in a relatively more proximal portion of the stretched cylindrical metal tube to provide relatively more bending flexibility in the relatively more distal portion of the stretched cylindrical metal tube than in the relatively more proximal portion of the stretched cylindrical metal tube.

6. The apparatus of claim 5, wherein a relatively more distal portion of the stretched cylindrical metal tube is stretched thinner than a relatively more proximal portion of the stretched cylindrical metal tube to yield wider laser cuts in the relatively more distal portion of the stretched cylindrical metal tube than in the relatively more proximal portion of the stretched cylindrical metal tube.

7. The apparatus of claim 3, wherein a relatively more distal portion of the stretched cylindrical metal tube is stretched with respect to a relatively more proximal portion of the stretched cylindrical metal tube to provide relatively more bending flexibility in the relatively more distal portion of the stretched cylindrical metal tube than in the relatively more proximal portion of the stretched cylindrical metal tube.

8. The apparatus of claim 3, wherein the inner body further comprises a liner within the tube along at least a portion of the tube to provide a desired lubricity to the inner working lumen of the sheath catheter, and in which a relatively more distal portion of the liner is stretched with respect to a relatively more proximal portion of the liner to provide relatively more bending flexibility in the relatively more distal portion of the liner than in the relatively more proximal portion of the liner.

9. The apparatus of claim 3, wherein the inner body includes:
  at least one of a metal braid or a metal coil in a more proximal region of the inner body than the tube;
  a polymer outer covering adjacent to the tube and adjacent to the at least one of a metal braid or a metal coil; and
  a liner within the tube along at least a portion of the tube to provide a desired lubricity to the inner working lumen of the sheath catheter, and wherein the polymer outer covering is reflowed to bond with the liner through engagement of the liner via a surface morphology of at least one of the tube or the braid.

10. The apparatus of claim 1, further comprising:
  a forward-viewing fiberoptic angioscope sized and shaped to be inserted from a proximal portion of the sheath catheter into the working lumen of the sheath catheter to allow a distal portion of the angioscope to be extended to, near, or beyond a distal opening of the working lumen of the sheath catheter to forwardly view and inspect a cerebrovascular pathology using the angioscope, wherein the angioscope comprises:
  a coherent fiber bundle of imaging optical fibers extending between proximal and distal portion of the angioscope, individual ones of the imaging fibers having an outer diameter of about 2.5 micrometers;
  an uncladded arrangement of illumination fibers, concentrically arranged around the imaging fibers, individual ones of the illumination fibers having an outer diameter between 25 micrometers and 50 micrometers; and
  wherein an outer diameter of the angioscope is less than or equal to 2.4 French.

11. The apparatus of claim 1, comprising a valve located toward a proximal portion of the sheath catheter, configured to allow a vacuum to be built up behind the valve and then applied to the working lumen of the sheath catheter upon opening the valve to permit sudden suction at a distal end of the working lumen of the sheath catheter.

12. The apparatus of claim 10, further comprising a cerebrovascular pathology treatment catheter sized and shaped to extend through the working lumen of the sheath catheter while allowing at least a portion of the angioscope to remain within the working lumen of the sheath catheter.

13. A cerebrovascular apparatus for at least partial insertion into a cerebrovasculature, the apparatus comprising:
  a sheath catheter, including:
  an elongate body, comprising an elongate outer body and an elongate inner body having a smaller outer periphery than an outer periphery of the outer body, an inflation lumen defined between the outer body and the inner body, an internal working lumen defined within the inner body, wherein the balloon is made of a compliant material configured to be expanded at a desired cerebrovascular location at which to stabilize the apparatus, and wherein the inner body includes a stretched cylindrical metal tube, including the stretching extending under the balloon, the stretching by between 50% and 200% inclusive, to inhibit collapse and maintain patency of the working lumen when an inflation pressure is applied to inflate the balloon;
  an inflatable balloon, located toward a distal portion of the elongate body of the sheath catheter; and
  wherein the inflation lumen extends between a proximal portion of the elongate body of the sheath catheter and the balloon to provide fluid communication to the balloon to permit inflation of the balloon; and
  wherein the working lumen extends between the proximal portion and the distal portion of the elongate body of the sheath catheter and the working lumen further extends to a distal tip of the sheath catheter that is offset by the internal world rig lumen being a single sidewall-hole-free closed-tubular-walled fluid-communicating suction lumen tube from a distal end of a distal cuff of the balloon by an offset distance of at least 8 millimeters and an outer diameter of less than 8 French to provide additional cerebrovascular access and suction beyond the balloon via the working lumen of the inner body.

14. The apparatus of claim 13, wherein the balloon is proximally attached to the elongate body of the sheath catheter via at least one of the outer periphery or distal face of the outer body, the balloon distally attached to the elongate body of the sheath catheter via at least the outer periphery of the inner body so as to be dimensionally stepped-down laterally relative to a more proximally attached portion of the distal cuff of the inflation balloon.

15. The apparatus of claim 13, wherein an inner lateral dimension of the working lumen at or near the distal tip of the sheath catheter flares outward in a distal direction to be larger than in a more proximal region of the working lumen.

16. The apparatus of claim 14, wherein a lateral outer dimension of an outer periphery of the distal tip of the sheath catheter flares outward in a distal direction to be equal to a lateral outer dimension of the outer periphery of the outer body of the sheath catheter at a location proximal to the balloon.

17. A cerebrovascular apparatus for at least partial insertion into a cerebrovasculature, the apparatus comprising:
  a sheath catheter, including:
  an elongate body, comprising an elongate outer body and an elongate inner body having a smaller outer periphery than an outer periphery of the outer body, an internal working lumen, defined within the inner body, that extends between a proximal portion and a distal portion of the elongate body of the sheath catheter; and
  wherein at least one of the inner body or the outer body includes a stretched cylindrical metal tube portion that is stretched by between 50% and 200% inclusive, including the stretching extending under the balloon, relative to another cylindrical metal tube portion of said at least one of the inner body or the outer body to provide greater relative bending flexibility in the stretched cylindrical metal tube portion relative to the another cylindrical metal tube portion.

18. The apparatus of claim 17, comprising:
an inflation lumen defined between the outer body and the inner body; and
an inflatable balloon, located toward a distal portion of the elongate body of the sheath catheter, wherein the inflation lumen extends between the proximal portion of the elongate body of the sheath catheter and the balloon to provide fluid communication to the balloon to permit inflation and deflation of the balloon, wherein the balloon is proximally attached to the elongate body of the sheath catheter via at least one of the outer periphery or distal face of the outer body, and wherein the balloon is distally attached to the elongate body of the sheath catheter via at least the outer periphery of the inner body so as to be dimensionally stepped-down laterally relative to a more proximally attached portion of a distal cuff of the inflation balloon, wherein the balloon is made of a compliant material configured to be expanded at a desired cerebrovascular location at which to stabilize the apparatus;
wherein the inner body comprises a stretched cylindrical metal tube, the stretching including extending under the balloon, the stretching by between 50% and 200% inclusive to inhibit collapse and maintain patency of the working lumen when an inflation pressure is applied to inflate the balloon; and
wherein a distal end of a distal cuff of the balloon is offset, by the internal working lumen being a single closed-tubular-walled fluid-communicating suction lumen tube, from a distal tip of the sheath catheter by an offset distance of at least 8 millimeters and an outer diameter of less than 8 French to provide additional cerebrovascular access and suction, beyond the balloon via the closed-tubular-walled suction lumen tube into the working lumen of the inner body to permit suctioning of a cerebrovascular clot via the closed-tubular-walled suction lumen.

19. The apparatus of claim 18, wherein the tube includes variable spacing laser cuts in the stretched cylindrical metal tube to increase its bending flexibility.

20. The apparatus of claim 19, including more closely spaced laser cuts in a relatively more distal portion of the stretched cylindrical metal tube than in a relatively more proximal portion of the stretched cylindrical metal tube to provide relatively more bending flexibility in the relatively more distal portion of the stretched cylindrical metal tube than in the relatively more proximal portion of the stretched cylindrical metal tube.

21. The apparatus of claim 20, wherein a relatively more distal portion of the stretched cylindrical metal tube is stretched thinner than a relatively more proximal portion of the stretched cylindrical metal tube to yield wider laser cuts in the relatively more distal portion of the stretched cylindrical metal tube than in the relatively more proximal portion of the stretched cylindrical metal tube.

22. The apparatus of claim 17, wherein a relatively more distal portion of the stretched cylindrical metal tube is stretched with respect to a relatively more proximal portion of the stretched cylindrical metal tube to provide relatively more bending flexibility in the relatively more distal portion of the stretched cylindrical metal tube than in the relatively more proximal portion of the stretched cylindrical metal tube.

23. The apparatus of claim 17, wherein the inner body further comprises a liner within the tube along at least a portion of the tube to provide a desired lubricity to the inner working lumen of the sheath catheter, in which a relatively more distal portion of the liner is stretched with respect to a relatively more proximal portion of the liner to provide relatively more bending flexibility in the relatively more distal portion of the liner than in the relatively more proximal portion of the liner.

24. A cerebrovascular apparatus for at least partial insertion into a cerebrovasculature, the apparatus comprising: a sheath catheter, including: an elongate body, comprising an elongate outer body and an elongate inner body having a smaller outer periphery than an outer periphery of the outer body, an internal working lumen, defined within the inner body, that extends between a proximal portion and a distal portion of the elongate body of the sheath catheter; an inflation lumen defined between the outer body and the inner body: and an inflatable balloon, located toward a distal portion of the elongate body of the sheath catheter, wherein the inflation lumen extends between the proximal portion of the elongate body of the sheath catheter and the balloon to provide fluid communication to the balloon to permit inflation and deflation of the balloon, wherein the balloon is proximally attached to the elongate body of the sheath catheter via at least one of the outer periphery or distal face of the outer body, and wherein the is balloon distally attached to the elongate body of the sheath catheter via at least the outer periphery of the inner body so as to be dimensionally stepped-down laterally relative to a more proximally attached portion of a distal cuff of the inflation balloon, wherein the balloon is made of a compliant material configured to be expanded at a desired cerebrovascular location at which to stabilize the apparatus, wherein the inner body includes a stretched cylindrical metal tube, including extending under the balloon, the stretching by between 50% and 200% inclusive, to inhibit collapse and maintain patency of the working lumen when an inflation pressure is applied to inflate the balloon, wherein the stretched cylindrical metal tube includes laser cuts to increase its bending flexibility; and wherein at least one of the inner body or the outer body includes at least a region having an inner portion and an outer portion that are bonded together via a reflow bond extending through a surface morphology, including the reflow bond extending through a plurality cut or braid openings through an intermediate portion located between the inner portion and the outer portion.

25. The apparatus of claim 24, including more closely spaced laser cuts in a relatively more distal portion of the stretched cylindrical metal tube than in a relatively more proximal portion of the stretched cylindrical metal tube to provide relatively more bending flexibility in the relatively more distal portion of the stretched cylindrical metal tube than in the relatively more proximal portion of the stretched cylindrical metal tube.

26. The apparatus of claim 25, wherein a relatively more distal portion of the stretched cylindrical metal tube is stretched thinner than a relatively more proximal portion of the stretched cylindrical metal tube to yield wider laser cuts in the relatively more distal portion of the stretched cylindrical metal tube than in the relatively more proximal portion of the stretched cylindrical metal tube.

* * * * *

UNITED STATES PATENT AND TRADEMARK OFFICE
CERTIFICATE OF CORRECTION

PATENT NO. : 11,399,711 B2
APPLICATION NO. : 17/359078
DATED : August 2, 2022
INVENTOR(S) : Cooper et al.

It is certified that error appears in the above-identified patent and that said Letters Patent is hereby corrected as shown below:

In the Claims

In Column 36, Line 49, in Claim 3, before "inhibit", insert --to--

In Column 38, Line 23, in Claim 13, delete "world rig" and insert --working-- therefor In Column 39, Line 34, in Claim 18, after "balloon", insert --,--

In Column 40, Line 26, in Claim 24, delete "is balloon" and insert --balloon is-- therefor Signed and Sealed this
Eleventh Day of October, 2022

Katherine Kelly Vidal
*Director of the United States Patent and Trademark Office*